(12) United States Patent
Gao et al.

(10) Patent No.: US 12,046,355 B2
(45) Date of Patent: Jul. 23, 2024

(54) METHOD AND SYSTEM FOR WEB-BASED MEDICAL IMAGE PROCESSING

(71) Applicant: Circle Cardiovascular Imaging Inc., Calgary (CA)

(72) Inventors: Xuexin Gao, Calgary (CA); Glen Paul Van De Mosselaer, Calgary (CA); Cynthia Mon-San Chiu, Calgary (CA); Qiao Wei, Calgary (CA)

(73) Assignee: Circle Cardiovascular Imaging Inc., Calgary (CA)

( * ) Notice: Subject to any disclaimer, the term of this patent is extended or adjusted under 35 U.S.C. 154(b) by 464 days.

(21) Appl. No.: 17/339,133

(22) Filed: Jun. 4, 2021

(65) Prior Publication Data

US 2022/0392615 A1 Dec. 8, 2022

(51) Int. Cl.
*G16H 80/00* (2018.01)
*G06F 16/904* (2019.01)
*G16H 10/00* (2018.01)
*G16H 15/00* (2018.01)
*G16H 30/20* (2018.01)
*G16H 30/40* (2018.01)

(52) U.S. Cl.
CPC .......... *G16H 30/40* (2018.01); *G06F 16/904* (2019.01); *G16H 30/20* (2018.01)

(58) Field of Classification Search
USPC ............... 358/1.1–3.29, 1.11–1.18, 405–406, 358/425–434; 382/128–253
See application file for complete search history.

(56) References Cited

U.S. PATENT DOCUMENTS

| | | |
|---|---|---|
| 6,934,698 B2 | 8/2005 | Judd et al. |
| 7,639,780 B2 | 12/2009 | Minyard et al. |
| 7,668,835 B2 | 2/2010 | Judd et al. |
| 7,958,100 B2 | 6/2011 | Judd et al. |
| 8,166,381 B2 | 4/2012 | Judd et al. |
| 8,553,965 B2 | 10/2013 | Zhao et al. |

(Continued)

OTHER PUBLICATIONS

Fitzgerald Daniel Liam; Content Compression for Network Transmission; Apr. 22, 2021 (Year: 2021).*

(Continued)

*Primary Examiner* — Marcellus J Augustin
(74) *Attorney, Agent, or Firm* — Taft Stettinius & Hollister LLP

(57) ABSTRACT

A medical imaging study comprising a plurality of medical images having been acquired by an imaging apparatus for a given patient are received, and a plurality of data arrays representing the plurality of medical images are generated. A request to display a given image is received from a client device. Benchmark testing with the client device is performed to obtain an indication of a performance of at least one of the client device and a communication link. A given compression algorithm from a set of compression algorithms is selected based on the indication of the performance, and used to compress a set of data arrays comprising a representation of the given image to obtain a set of compressed arrays. The set of compressed arrays are transmitted to the client device, the set of compressed arrays comprising the representation of the given image to be generated by a browser application.

21 Claims, 11 Drawing Sheets

(56) References Cited

U.S. PATENT DOCUMENTS

| | | | |
|---|---|---|---|
| 8,630,501 B1* | 1/2014 | Fram | H04N 19/174 |
| | | | 386/328 |
| 9,667,696 B2 | 5/2017 | Hu et al. | |
| 9,917,868 B2 | 3/2018 | Ahmed | |
| 2012/0191793 A1 | 7/2012 | Jakobovits | |
| 2014/0143298 A1 | 5/2014 | Klotzer et al. | |
| 2014/0279944 A1* | 9/2014 | Ghandeharizadeh | |
| | | | G06F 16/2365 |
| | | | 707/690 |
| 2015/0074181 A1 | 3/2015 | Taerum et al. | |
| 2015/0347682 A1 | 12/2015 | Chen et al. | |
| 2017/0178266 A1 | 6/2017 | Schmidt | |
| 2019/0304590 A1* | 10/2019 | Wilson | G16H 30/20 |
| 2019/0335096 A9 | 10/2019 | Westin et al. | |

OTHER PUBLICATIONS

Vincent Brigil; Image Viewer; Feb. 17, 2020 (Year: 2020).*
Sugimoto Kenji; Video Conversion System and Video Conversion Method; Nov. 25, 2004 (Year: 2004).*
Ebrahimi Houman; System, Method and Interface for Communication and Viewing of Medical Imaging; 2020 (Year: 2020).*
Netlify; Ohif (Open Health Imaging Foundation) Introduction; https://docs.ohif.org; 1 page.
Box Support; Using Box DICOM; https://support.box.com/hc/en-us/articles/1500005812782-Using-Box-DICOM; Apr. 1, 2021; 2 pages.
Fovia; F.A.S.T. Cloud Sdk; Create Zero-Footprint Viewers with our 3D Application Developer Tools; https://www.fovia.com/cloud-sdk/; 9 pages; Copyright 2021 Fovia, Inc.

* cited by examiner

METHOD AND SYSTEM FOR WEB-BASED MEDICAL IMAGE PROCESSING

FIELD

The present technology pertains to the field of medical imaging. More specifically, the present technology relates to a method and a system for web-based medical imaging processing.

BACKGROUND

In recent years, with the technological improvements in network speed and mobile computing power, web-based software systems for medical imaging workflow have gained popularity in the healthcare industry due to the superior accessibility they provide compared to traditional desktop-based medical imaging software. For example, such web-based imaging systems are used as standard tools in teleradiology scenarios, where physicians can access collaborative imaging workflows with portable devices from anywhere without the need to be physically present in reading rooms and/or in front of an imaging workstation. The superior accessibility, in turn, translates to enhanced and efficient patient outcomes.

However, given the nature of such distributed systems, their performance is often affected by many factors including network bandwidth, hardware specifications, etc. For example, for server-side image rendering operations that are performed using a central server, the system's ability to serve multiple users concurrently may be challenged. On the other hand, when client-side rendering operations are required, a low network bandwidth may cause slow data transfer rate and unacceptable user experience. Those drawbacks could be amplified if the imaging workflow is in the acute setting, where being able to see images during the imaging process or after the imaging process may be crucial. One such example is the acute stroke computational tomography (CT) imaging scenario, where every minute of delay could cause a loss of 2 million neurons in a patient's brain.

In addition to performance drawbacks, some web-based medical imaging software also trade off persistency for accessibility, as well as reusability for security. Due to their zero-footprint nature, web-based software, unlike desktop solutions, lack the functionality to persist some data on the client machine. For example, on a desktop software, a certain of the image data could be temporarily saved to the file system for reuse even if the software is closed or if the computing device is shut down. When certain data needs to be reused, retrieving such data from local file system has an optimal speed. On the contrary, for web-based software, once the browser is closed, all user session related data, including the image and other log information is cleared from the client device. In this scenario, if a user wants to reopen the same image, the same amount of data will need to be transferred from the server to the client, hence introducing inefficiency.

SUMMARY

It is an object of the present technology to ameliorate at least some of the inconveniences present in the prior art. One or more embodiments of the present technology may provide and/or broaden the scope of approaches to and/or methods of achieving the aims and objects of the present technology.

Developers of the present technology have appreciated that there is a need for a collaborative medical analysis workflow that can be executed in a web browser application, which can remotely connect to one or more server(s) that connect to scanner devices and/or medical image archiving systems, and which provide optimized real-time user experiences.

One or more embodiments of the present technology have been developed based on developers' appreciation that optimized user experience could be provided by leveraging client and server hardware, user interactions, and workflow conditions for performing data transmission. Benchmark techniques could be used to assess the performance of the system for data compression and data transmission, and to determine if data compression is worthwhile when images are requested to minimize the user idle time.

Further, developers have appreciated that a hybrid client-side and server-side rendering approach for 3D image rendering could be provided for an optimal use of available resources on both client device and server. Once a web-based client receives all the image data for building the 3D image, the usage of computing power of the client device for performing 3D image rendering could be maximized. However, during image transfer, to minimize user idle time, the server may render the requested 3D image view which is currently requested by the user and provide the rendered frame to the user for display while image transfer is completed, which enables the client device to then render the requested 3D image view. Therefore, one or more embodiments of the present technology may provide instantaneous response to the user by leveraging both client-side and server-side computing power dynamically.

Thus, one or more embodiments of the present technology are directed to a method of and system for web-based medical image processing.

In accordance with a broad aspect of the present technology, there is provided a method for displaying a medical image on a client device connected to a server via communication link over communication network. The method comprises: receiving, by the server, a medical imaging study including a plurality of medical images having been acquired by a medical imaging apparatus for a given patient, generating, by the server, for each image of the plurality of images in the medical imaging study, a respective data array to obtain a plurality of data arrays, receiving, by the server from the client device, a request to display a given image of the medical image study, performing benchmark testing with the client device to obtain an indication of a performance of at least one of the client device and the communication link, selecting, based on the indication of the performance of the at least one of the client device and the communication link, a given compression algorithm from a set of compression algorithms, compressing, by using the given compression algorithm, a set of data arrays including a representation of the given image to obtain a set of compressed arrays, and transmitting, to the client device, the set of compressed arrays, the set of compressed arrays including the representation of the given image to be generated for display on the client device.

In one or more embodiments of the method, the performing the benchmark testing with the client device comprises: generating, by the server, a test array, the test array having a first size and is associated with a first timestamp, compressing, by the server, using one of the set of compression algorithms, the test array to obtain a compressed test array, the compressed test array having a second size is associated with a second timestamp, transmitting, by the server to the client device, the compressed test array, receiving, by the server from the client device, an indication of a decompressed test data array, the indication of the test data array is associated with a third timestamp, and determining, based on the first timestamp, the second timestamp, the third timestamp, the first size and the second size, the indication of the performance of the at least one of the client device and the communication link.

In one or more embodiments of the method, the determining the indication of the performance of the at least one of the client device and the communication link comprises: determining a transmission speed based on the second size, the third timestamp and the second timestamp, determining a compressed roundtrip time based on the third timestamp and the first timestamp, and determining an uncompressed roundtrip time based on the first size, the third timestamp and the first timestamp.

In one or more embodiments of the method, the method further comprises, prior to said transmitting, to the client device, the set of compressed array including the representation of the given image: receiving past user interaction data from a database connected to the server, and selecting, based on the past user interaction data, the set of compressed arrays from the plurality of compressed arrays, the set of compressed arrays including a representation of at least one other image not having been explicitly requested by the client device.

In one or more embodiments of the method, the past user interaction data comprises at least one of: past user interaction data of a user of the client device, past interaction data related to the given patient, and past interaction data related to similar medical imaging studies having been previously interacted with.

In one or more embodiments of the method, the method further comprises: receiving, by the server, from the client device, a request for displaying a multi-dimensional visualization of at least a portion of the medical imaging study, determining, by the server, based on the request, a set of medical images required for generating the multi-dimensional visualization, transmitting, by the server to the client device, at least a portion of a further set of data arrays, the further set of data arrays including a representation of the set of medical images required for generating the multi-dimensional visualization on the client device, determining a current performance of at least one of the client device and the communication link, and in response to the current performance of at least one of the client device and the communication link is below a performance threshold: generating, by the server, the multi-dimensional visualization of the medical imaging study, generating a further data array including a representation at least one rendered frame of the multi-dimensional visualization of the medical imaging study, and transmitting, by the server to the client device, the further data array including the representation of the at least one frame of the multi-dimensional visualization of the medical imaging study for display on the client device.

In one or more embodiments of the method, the method further comprises: transmitting, by the server, to the client device, a remainder of the further set of data arrays, the transmitting thereby causing the client device to generate the multi-dimensional visualization of the medical imaging study using the further set of data arrays.

In one or more embodiments of the method, said transmitting, by the server to the client device, at least the portion of the further set of data arrays comprises: compressing, by using the given compression algorithm, at least the portion of the further set of data arrays to obtain compressed further data arrays.

In one or more embodiments of the method, the request for displaying the multi-dimensional visualization of the medical imaging study comprises a scene information and a camera setting, and said determining the set of medical images required for generating the multi-dimensional visualization is based on the scene information and the camera setting.

In one or more embodiments of the method, said determining a current performance of at least one of the client device and the communication link respectively comprises: determining available computational resources on the client device, determining a transmission time, and determining a transmission speed.

In one or more embodiments of the method, the respective data array comprises a respective pixel array.

In one or more embodiments of the method, said transmitting, to the client device, the set of compressed arrays comprises marshalling the set of compressed arrays to obtain a set of binary serialized compressed arrays and transmitting the set of binary serialized compressed arrays to the client device.

In one or more embodiments of the method, the medical imaging study is a DICOM file including a header portion and an imaging portion, and said generating for each image in the medical imaging study, the respective data array is based on the imaging portion.

In one or more embodiments of the method, the client device executes a browser application for displaying medical images.

In one or more embodiments of the method, the browser application is configured to generate the given medical image for display by using a canvas element.

In one or more embodiments of the method, the given medical image is a lossless image.

In accordance with a broad aspect of the present technology, there is provided a system comprising a processor, and a non-transitory storage medium operatively connected to the processor, the non-transitory storage medium storing computer-readable instructions thereon, the system being connected to a client device via a communication link over a communication network, the processor upon executing the instructions, being configured for: receiving a medical imaging study including a plurality of medical images having been acquired by a medical imaging apparatus for a given patient, generating for each image of the plurality of images in the medical imaging study, a respective data array to obtain a plurality of data arrays, receiving, from the client device, a request to display a given image of the medical image study, performing benchmark testing with the client device to obtain an indication of a performance of at least one of the client device and the communication link, selecting, based on the indication of the performance of the at least one of the client device and the communication link, a given compression algorithm from a set of compression algorithms, compressing, by using the given compression algorithm, a set of data arrays including a representation of the given image to obtain a set of compressed arrays, and transmitting, to the client device, the set of compressed arrays, the set of compressed arrays including the representation of the given image to be generated for display on the client device.

In one or more embodiments of the system, the performing the benchmark testing with the client device comprises: generating, a test array, the test array having a first size and being associated with a first timestamp, compressing, using one of the set of compression algorithms, the test array to obtain a compressed test array, the compressed test array having a second size is associated with a second timestamp, transmitting, to the client device, the compressed test array, receiving, from the client device, an indication of a decompressed test data array, the indication of the test data array being associated with a third timestamp, and determining, based on the first timestamp, the second timestamp, the third timestamp, the first size and the second size, the indication of the performance of the at least one of the client device and the communication link.

In one or more embodiments of the system, the determining the indication of the performance of the at least one of the client device and the communication link comprises: determining a transmission speed based on the second size, the third timestamp and the second timestamp, determining a compressed roundtrip time based on the third timestamp and the first timestamp, and determining an uncompressed roundtrip time based on the first size, the third timestamp and the first timestamp.

In one or more embodiments of the system, the processor is further configured for, prior to said transmitting, to the client device, the set of compressed array including the representation of the given image: receiving past user interaction data from a database connected to the server, and selecting, based on the past user interaction data, the set of compressed arrays from the plurality of compressed arrays, the set of compressed arrays including a representation of at least one other image not having been explicitly requested by the client device.

In one or more embodiments of the system, the past user interaction data comprises at least one of: past user interaction data of a user of the client device, past interaction data related to the given patient, and past interaction data related to similar medical imaging studies having been previously interacted with.

In one or more embodiments of the system, the processor is further configured for: receiving, from the client device, a request for displaying a multi-dimensional visualization of at least a portion of the medical imaging study, determining, based on the request, a set of medical images required for generating the multi-dimensional visualization, transmitting, to the client device, at least a portion of a further set of data arrays, the further set of data arrays including a representation of the set of medical images required for generating the multi-dimensional visualization on the client device, determining a current performance of at least one of the client device and the communication link, and in response to the current performance of at least one of the client device and the communication link is below a performance threshold: generating, the multi-dimensional visualization of the medical imaging study, generating a further data array including a representation at least one rendered frame of the multi-dimensional visualization of the medical imaging study, and transmitting, to the client device, the further data array including the representation of the at least one frame of the multi-dimensional visualization of the medical imaging study for display on the client device.

In one or more embodiments of the system, the processor is further configured for: transmitting, to the client device, a remainder of the further set of data arrays, the transmitting thereby causing the client device to generate the multi-dimensional visualization of the medical imaging study using the further set of data arrays.

In one or more embodiments of the system, said transmitting, to the client device, at least the portion of the further set of data arrays comprises: compressing, by using the given compression algorithm, at least the portion of the further set of data arrays to obtain compressed further data arrays.

In one or more embodiments of the system, the request for displaying the multi-dimensional visualization of the medical imaging study comprises a scene information and a camera setting, and said determining the set of medical images required for generating the multi-dimensional visualization is based on the scene information and the camera setting.

In one or more embodiments of the system, said determining a current performance of at least one of the client device and the communication link respectively comprises: determining available computational resources on the client device, determining a transmission time, and determining a transmission speed.

In one or more embodiments of the system, the respective data array comprises a respective pixel array.

In one or more embodiments of the system, said transmitting, to the client device, the set of compressed arrays comprises marshalling the set of compressed arrays to obtain a set of binary serialized compressed arrays and transmitting the set of binary serialized compressed arrays to the client device.

In one or more embodiments of the system, the medical imaging study is a DICOM file including a header portion and an imaging portion, and said generating for each image in the medical imaging study, the respective data array is based on the imaging portion.

In one or more embodiments of the system, the client device executes a browser application for displaying medical images.

In one or more embodiments of the system, the browser application is configured to generate the given medical image for display by using a canvas element.

In one or more embodiments of the system, the given medical image is a lossless image.

Terms and Definitions

In the context of the present specification, a "server" is a computer program that is running on appropriate hardware and is capable of receiving requests (e.g., from electronic devices) over a network (e.g., a communication network), and carrying out those requests, or causing those requests to be carried out. The hardware may be one physical computer or one physical computer system, but neither is required to be the case with respect to the present technology. In the present context, the use of the expression "a server" is not intended to mean that every task (e.g., received instructions or requests) or any particular task will have been received, carried out, or caused to be carried out, by the same server (i.e., the same software and/or hardware); it is intended to mean that any number of software elements or hardware devices may be involved in receiving/sending, carrying out or causing to be carried out any task or request, or the consequences of any task or request; and all of this software and hardware may be one server or multiple servers, both of which are included within the expressions "at least one server" and "a server".

In the context of the present specification, "electronic device" is any computing apparatus or computer hardware that is capable of running software appropriate to the relevant task at hand. Thus, some (non-limiting) examples of electronic devices include general purpose personal computers (desktops, laptops, netbooks, etc.), mobile computing devices, smartphones, and tablets, and network equipment such as routers, switches, and gateways. It should be noted that an electronic device in the present context is not precluded from acting as a server to other electronic devices. The use of the expression "an electronic device" does not preclude multiple electronic devices being used in receiving/sending, carrying out or causing to be carried out any task or request, or the consequences of any task or request, or steps of any method described herein. In the context of the present specification, a "client device" refers to any of a range of end-user client electronic devices, associated with a user, such as personal computers, tablets, smartphones, and the like.

In the context of the present specification, the expression "computer readable storage medium" (also referred to as "storage medium" and "storage") is intended to include non-transitory media of any nature and kind whatsoever, including without limitation RAM, ROM, disks (CD-ROMs, DVDs, floppy disks, hard drivers, etc.), USB keys, solid state-drives, tape drives, etc. A plurality of components may be combined to form the computer information storage media, including two or more media components of a same type and/or two or more media components of different types.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus, information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document could include the document itself (i.e. its contents), or it could be a unique document descriptor identifying a file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the expression "communication network" is intended to include a telecommunications network such as a computer network, the Internet, a telephone network, a Telex network, a TCP/IP data network (e.g., a WAN network, a LAN network, etc.), and the like. The term "communication network" includes a wired network or direct-wired connection, and wireless media such as acoustic, radio frequency (RF), infrared and other wireless media, as well as combinations of any of the above.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "server" and "third server" is not intended to imply any particular order, type, chronology, hierarchy or ranking (for example) of/between the servers, nor is their use (by itself) intended to imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
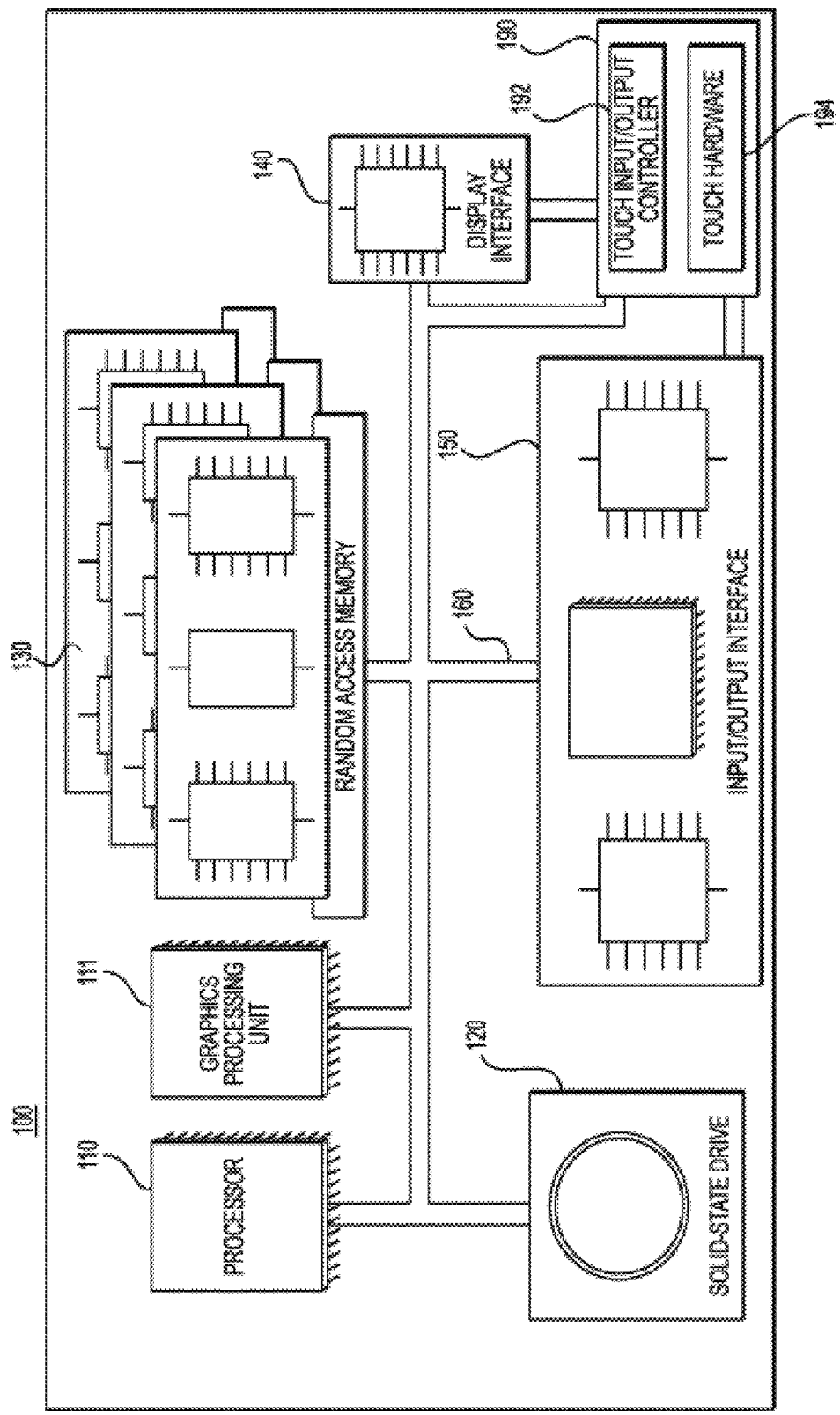
FIG. 1 depicts a schematic diagram of an electronic device in accordance with one or more non-limiting embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some non-limiting embodiments of the present technology, the processor may be a general-purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

With reference to FIG. 1, there is illustrated a schematic diagram of an electronic device 100 suitable for use with some non-limiting embodiments of the present technology.

Electronic Device

The electronic device 100 comprises various hardware components including one or more single or multi-core processors collectively represented by processor 110, a graphics processing unit (GPU) 111, a solid-state drive 120, a random-access memory 130, a display interface 140, and an input/output interface 150.

Communication between the various components of the electronic device 100 may be enabled by one or more internal and/or external buses 160 (e.g. a PCI bus, universal serial bus, IEEE 1394 "Firewire" bus, SCSI bus, Serial-ATA bus, etc.), to which the various hardware components are electronically coupled.

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 2, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the electronic device 100 in addition or in replacement of the touchscreen 190.

According to implementations of the present technology, the solid-state drive 120 stores program instructions suitable for being loaded into the random-access memory 130 and executed by the processor 110 and/or the GPU 111 for performing web-based medical image processing.

The electronic device 100 may be implemented in the form of a server, a desktop computer, a laptop computer, a tablet, a smartphone, a personal digital assistant or any device that may be configured to implement the present technology, as it may be understood by a person skilled in the art.

System

Figure 2:
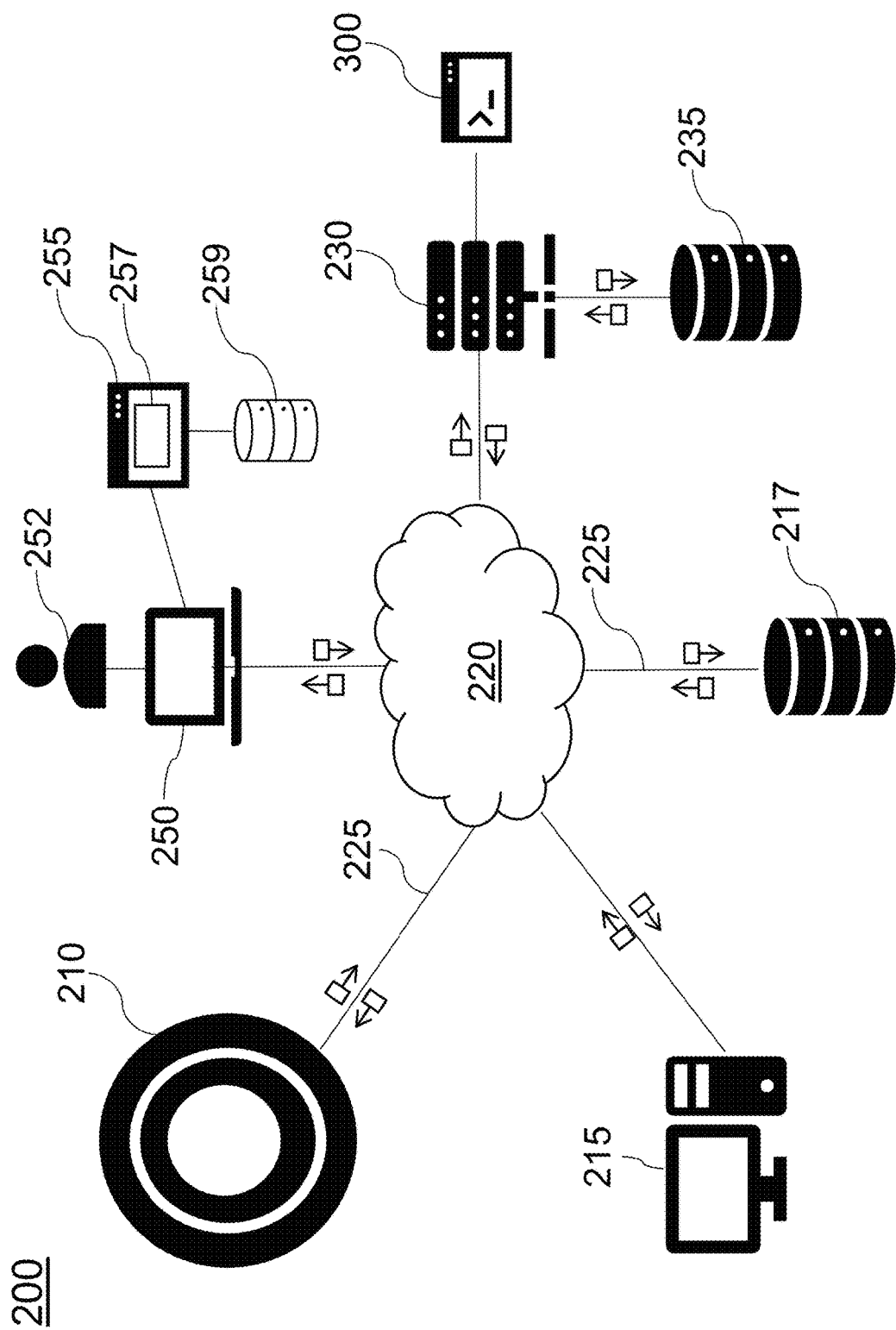
FIG. 2 depicts a schematic diagram of a system in accordance with one or more non-limiting embodiments of the present technology.

Referring to FIG. 2, there is shown a schematic diagram of a communication system 200, which will be referred to as the system 200, the system 200 being suitable for implementing non-limiting embodiments of the present technology. It is to be expressly understood that the system 200 as illustrated is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 200 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition it is to be understood that the system 200 may provide in certain instances simple implementations of the present technology, and that where such is the case they have been presented in this manner as an aid to understanding. As persons skilled in the art would understand, various implementations of the present technology may be of a greater complexity.

The system 200 is configured to provide a web-based software for assisting the imaging analysis for the diagnosis and the treatment of patients. Specifically, the system allows a collaborative medical analysis workflow to be performed on a web browser, which remotely connected to a server(s) that connects to scanner devices or medical image archiving systems, with optimized real-time user experiences.

The system 200 comprises inter alia a medical imaging apparatus 210 associated with a workstation computer 215 and a picture archiving and communication system (PACS) database 217, a server 230 associated with a database 235 and a client device 250 coupled over a communications network 220 via respective communication links 225 (not separately numbered).

Medical Imaging Apparatus

The medical imaging apparatus 210 is configured to inter alia: (i) acquire, based on a set of imaging parameters, a set of medical images of a subject; and (ii) transmit the set of medical images of the subject to one or more of the workstation computer 215, the PACS database 217, and/or the server 230.

The nature of the medical imaging apparatus 210 is not limited, and the medical imaging apparatus 210 may comprise one or more of: an ultrasound (US) apparatus, a magnetic resonance (MR), a Nuclear Medicine imaging, a positron emission tomography (PET), a computed tomography (CT), endoscopy (ES), mammograms (MG), digital radiography (DR), and phosphor plate radiography.

The medical imaging apparatus 210 may generate, measures and record one or more different kinds of acquired imaging data concerning an imaged subject or object. In one or more embodiments, the medical imaging apparatus 210 has an imaging processing component which receives the acquired imaging data and, in some cases, processes it to generate reconstructed imaging data which can be viewed on a display. In other cases, such post-acquisition processing may not be necessary in order to display the imaging data for review by users, or it might be performed at a later time by a different system such as the workstation computer 215.

Depending on the type of medical imaging apparatus 210, acquisition parameters such as one or more of intensity, time, length, radiation dose, and the like may be specified by an operator directly via an input/output interface (not depicted) on the medical imaging apparatus 210 or via the workstation computer 215 for example. Upon acquiring a set of medical images or study of a patient, the medical imaging apparatus 210 is configured to transmit the study to one or more of the workstation computer 215, the PACS database 217, and/or the server 230. It will be appreciated that the communication link between the medical imaging apparatus 210 and any other apparatus connected thereto may be a wired or wireless communication link.

Workstation Computer

The workstation computer 215 is configured to inter alia: (i) control acquisition parameters of the medical imaging apparatus 210 and cause the medical imaging apparatus 210 to acquire images; (ii) receive and process the plurality of images from the medical imaging apparatus 210; and (iii) store the images in the PACS database 217.

In one or more embodiments, the workstation computer 215 may receive images in raw format and apply known image reconstruction techniques to process the acquired images and reconstruct imaging data comprising digital images of the imaged patient or other object. In one or more embodiments, the workstation computer 215 may perform 2D visualization and 3D visualization of the acquired images and/or the reconstructed medical images to medical personnel.

The implementation of the workstation computer 215 is known in the art. The workstation computer 215 may be implemented as the electronic device 100 or comprise components thereof, such as the processor 110, the graphics processing unit (GPU) 111, the solid-state drive 120, the random-access memory 130, the display interface 140, and the input/output interface 150.

In one or more other embodiments, the workstation computer 215 may be integrated at least in part into the medical imaging apparatus 210.

In one or more embodiments, the workstation computer 215 may be operatively connected to a Picture Archiving and Communication Systems (PACS) database 217 and may be configured according to according to the Digital Imaging and Communications in Medicine (DICOM) standard for communication and management of medical imaging information and related data. The workstation computer 215 may access metadata and image data from the PACS database 217 using a DICOM query protocol, and share information using a DICOM communications protocol.

It will be appreciated that the DICOM Standard facilitates interoperability of medical imaging equipment by specifying: (i) for network communications, a set of protocols to be followed by devices claiming conformance to the standard; (ii) the syntax and semantics of commands and associated information that can be exchanged using these protocols; (iii) for media communication, a set of media storage services to be followed by devices claiming conformance to the standard, as well as a file format and a medical directory structure to facilitate access to the images and related information stored on interchange media; and (iv) information that must be supplied with an implementation for which conformance to the standard is claimed.

In one or more embodiments, the workstation computer 215 may store the images in the PACS database 217.

PACS Database

The PACS database 217 is communicatively coupled to the medical imaging apparatus 210 via the communications network 220 but, in one or more alternative implementations, the PACS database 217 may be directly connected to the medical imaging apparatus 210 without departing from the teachings of the present technology. Although the PACS database 217 is illustrated schematically herein as a single entity, it will be appreciated that the PACS database 217 may be configured in a distributed manner, for example, the PACS database 217 may have different components, each component being configured for a particular kind of retrieval therefrom or storage therein.

The PACS database 217 may be a structured collection of data, irrespective of its particular structure or the computer hardware on which data is stored, implemented or otherwise rendered available for use. The PACS database 217 may reside on the same hardware as a process that stores or makes use of the information stored in the PACS database 217 such as the workstation computer 215, or it may reside on separate hardware, such as on one or more other electronic devices (not shown) directly connected to the server 230 and/or connected to the communications network 220. The database 235 may receive data from the medical imaging apparatus 210 for storage thereof and may provide stored data to the workstation computer 215 for use thereof.

In the context of the present technology, a DICOM file comprises a header portion and an imaging data portion.

The imaging data portion stores the imaging data, i.e., the two-dimensional or three-dimensional matrix of intensity or other values which define a pixilated or voxelated image. This data corresponds for example to different views of a digital imaging display. The header portion stores information related to the imaging data portion. Other file formats use a similar header/image data format.

The header portion stores identification information. The identification information might include, for example, the name of the patient being imaged. The identification information in the header portion also might include demographic information concerning the patient, such as for example patient id, patient's name, patient's birth date, patient's sex, patient's size, patient's weight, patient comments, institution name, institution address, referring physician's name, performing physician's name, and the like. The identification information also might include image acquisition information concerning the imaging data, such as for example the type of the medical imaging apparatus 210 (CT, PET, etc.), the duration of the imaging acquisition, the current applied to the x-ray tube for a transmission x-ray imaging acquisition, the type of radiopharmaceutical used for an emission imaging acquisition, the pixel or voxel matrix size of the reconstructed imaging data, and the like. The identification information also might include image processing information, concerning how the acquired imaging data was processed to generate reconstructed imaging data stored in portion. Under the DICOM standard, the header portion also includes a portion of non-dedicated or free memory which may be used by a particular user to store any information defined by that user. In that way, the DICOM standard permits some limited user customization to the types of identification information stored in the header portion.

The PACS database 217 is configured to inter alia: (i) receive DICOM files from the medical imaging apparatus 210; (ii) store the DICOM files; and (iii) retrieve and provide the DICOM files to one or more of the workstation computer 215, the server 230 and the client device 250.

Server

The server 230 is configured to inter alia: (i) communicate with one or more of the medical imaging apparatus 210, the workstation computer 215 and the client device 250 by receiving data and transmitting data; and (ii) provide a medical imaging viewing service 300 accessible by client devices such as the client device 250.

The server 230 may be located inside our outside of a hospital and is configured to use a web-based bi-directional communication system (Web Sockets) with client devices such as the client device 250.

How the server 230 is configured to do so will be explained in more detail herein below.

The server 230 can be implemented as a conventional computer server and may comprise some or all of the components of the electronic device 100 illustrated in FIG. 2. In an example of one or more embodiments of the present technology, the server 230 can be implemented as a Dell™ PowerEdge™ Server running the Microsoft™ Windows Server™ operating system. Needless to say, the server 230 can be implemented in any other suitable hardware and/or software and/or firmware or a combination thereof. In the illustrated non-limiting embodiment of present technology, the server 230 is a single server. In alternative non-limiting embodiments of the present technology, the functionality of the server 230 may be distributed and may be implemented via multiple servers (not illustrated).

The implementation of the server 230 is well known to the person skilled in the art of the present technology. However, briefly speaking, the server 230 comprises a communication interface (not illustrated) structured and configured to communicate with various entities (such as the workstation computer 215, for example and other devices potentially coupled to the network 220) via the communications network 220. The server 230 further comprises at least one computer processor (e.g., a processor 110 or GPU 111 of the electronic device 100) operationally connected with the communication interface and structured and configured to execute various processes to be described herein.

In one or more embodiments, the server 230 may be implemented as the electronic device 100 or comprise components thereof, such as the processor 110, the graphics processing unit (GPU) 111, the solid-state drive 120, the random-access memory 130, the display interface 140, and the input/output interface 150.

Database

The database 235 is directly connected to the server 230 but, in one or more alternative implementations, the database 235 may be communicatively coupled to the server 230 via the communications network 220 without departing from the teachings of the present technology. Although the database 235 is illustrated schematically herein as a single entity, it will be appreciated that the database 235 may be configured in a distributed manner, for example, the database 235 may have different components, each component being configured for a particular kind of retrieval therefrom or storage therein.

The database 235 may be a structured collection of data, irrespective of its particular structure or the computer hardware on which data is stored, implemented or otherwise rendered available for use. The database 235 may reside on the same hardware as a process that stores or makes use of the information stored in the database 235 such as the server 230, or it may reside on separate hardware, such as on one or more other electronic devices (not shown) directly connected to the server 230 and/or connected to the communications network 220. The database 235 may receive data from the server 230 for storage thereof and may provide stored data to the server 230 for use thereof.

In one or more embodiments, the database 235 may be implemented as a NoSQL database such as MongoDB and/or SQL database such as Microsoft SQL Server.

The database 235 is configured to inter alia: (i) store DICOM files or information related thereto and/or extracted therefrom; (ii) store information related to the medical imaging viewing service 300; (iii) store performance data related to the server 230, the client device 250, the communication network and the communication link 225; and (iii) store user interaction data performed by the user 252 of the client device 250 and other users of the medical imaging viewing service 300.

Client Device

The system 200 comprises a client device 250. The client device 250 is associated with the user 252. As such, the client device 250 can sometimes be referred to as a "electronic device", "end user device" or "client electronic device".

The client device 250 comprises one or more components of the electronic device 100 such as one or more single or multi-core processors collectively represented by processor 110, the graphics processing unit (GPU) 111, the solid-state drive 120, the random access memory 130, the display interface 140, and the input/output interface 150.

In one or more embodiments, the client device 250 is configured to execute a browser application 255.

The browser application 255 is configured to receive and to send web pages, web-based messages, and the like. The browser application may be configured to receive and display graphics, text, multimedia, or the like, employing virtually any web based language, including a wireless application protocol messages (WAP), or the like. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), or the like, to display and send information.

In one or more embodiments, the browser application 255 maintains a memory cache 259. It will be appreciated that the memory cache 259 of the browser application 255 may use the storage medium of the client device 250. The browser application 255 is configured to implement Most-Recently-Used (MRU) and Least-Recently-Used (LRU) cache-expiration logic for the storage of the binary data to make sure the storage of the client device 250 is maintained within a reasonable size limit (e.g. below a set threshold determined by the user 252 or by the server 230).

In one or more embodiments, the browser application 255 is configured to employ HTML5 and Javascript.

How the given browser application 255 is implemented is not particularly limited. Non-limiting examples of the given browser application that is executable by the client device 250 include Google™ Chrome™, Mozilla™ Firefox™, Microsoft™ Edge™ and Apple™ Safari™.

In the context of the present technology, the browser application 255 is configured to access the medical imaging viewing service 300 provided by the server 220 via the client-side medical imaging viewer 257. In one or more alternative embodiments, the client-side medical imaging viewer 257 may be provided as a software application on the client device 250.

In one or more embodiments the client-side medical imaging viewer 257 may be accessible via a uniform resource locator (URL) on the browser application 255. The user 252 may provide login information to access the client-side medical imaging viewer 257. For example, the user 252 may be a radiologist wishing to access images captured by the medical imaging apparatus 210 on the client device 250. The user 252 may use the browser application 255 to access the client-side medical imaging viewer 257.

Figure 7:
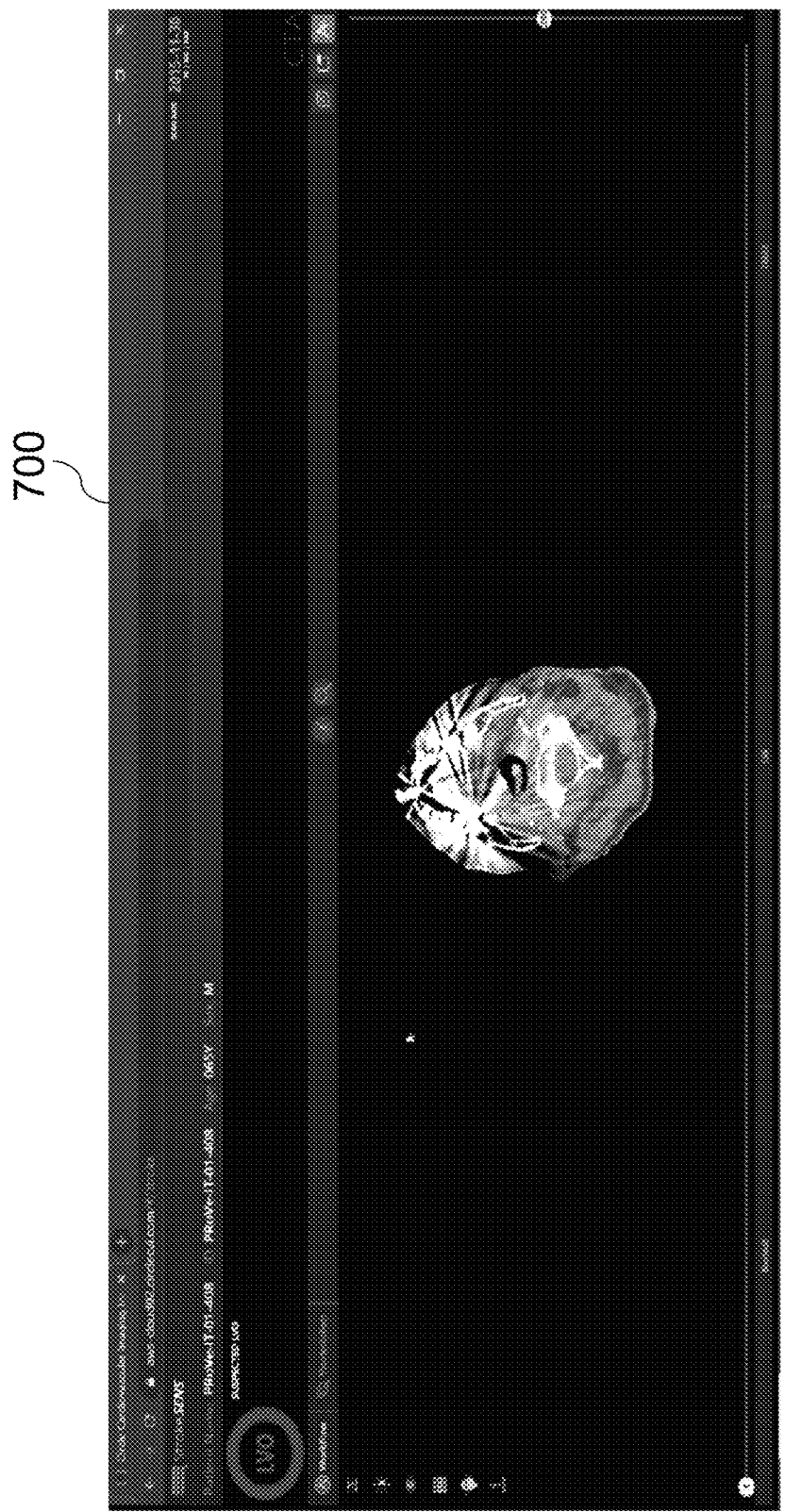
FIG. 7 depicts a screenshot of a graphical user interface (GUI) displaying a medical image on the client-side medical image viewer in accordance with one or more non-limiting embodiments of the present technology.
Figure 8:
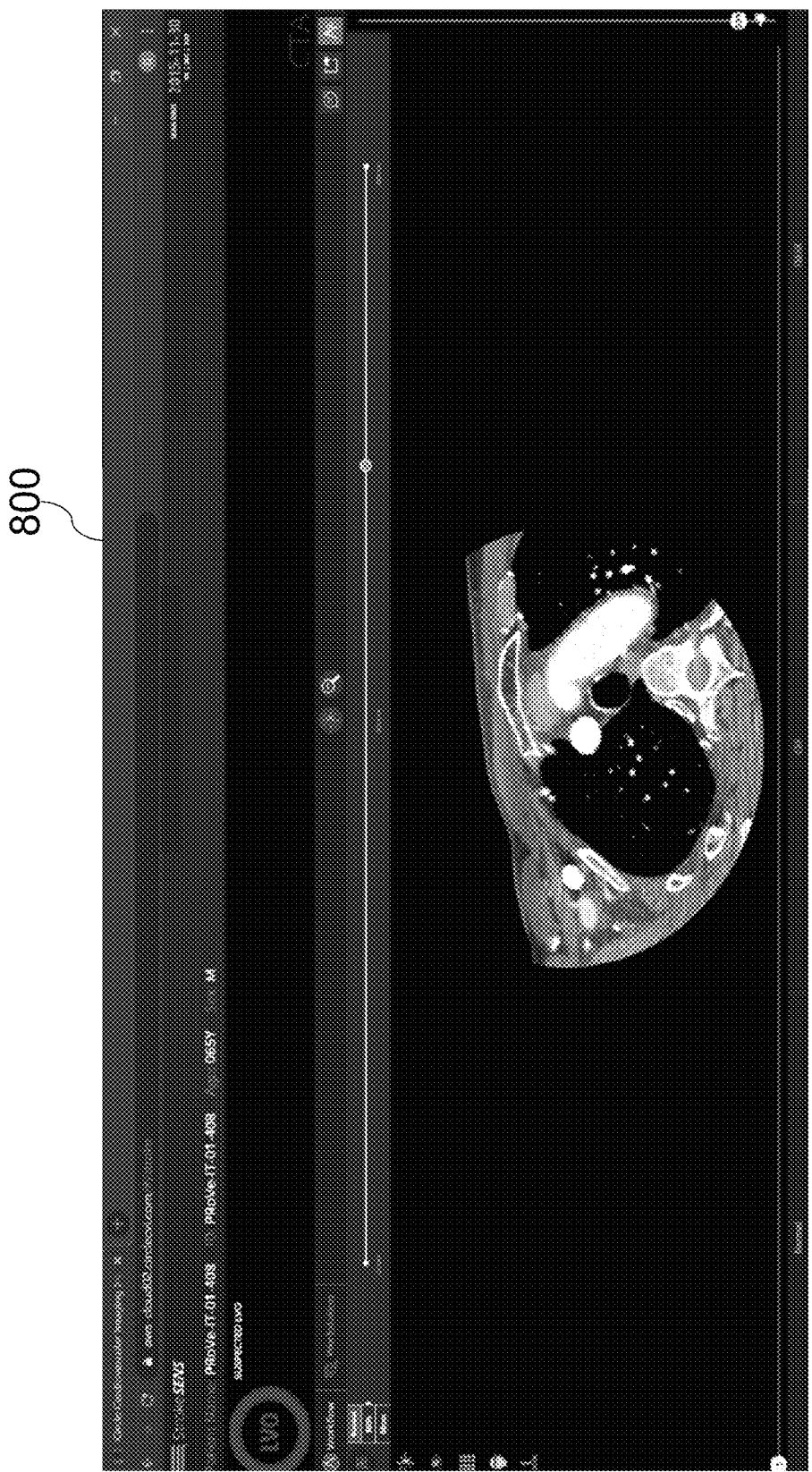
FIG. 8 depicts another screenshot of a graphical user interface (GUI) displaying a medical image on the client-side medical image viewer in accordance with one or more non-limiting embodiments of the present technology.
Figure 9:
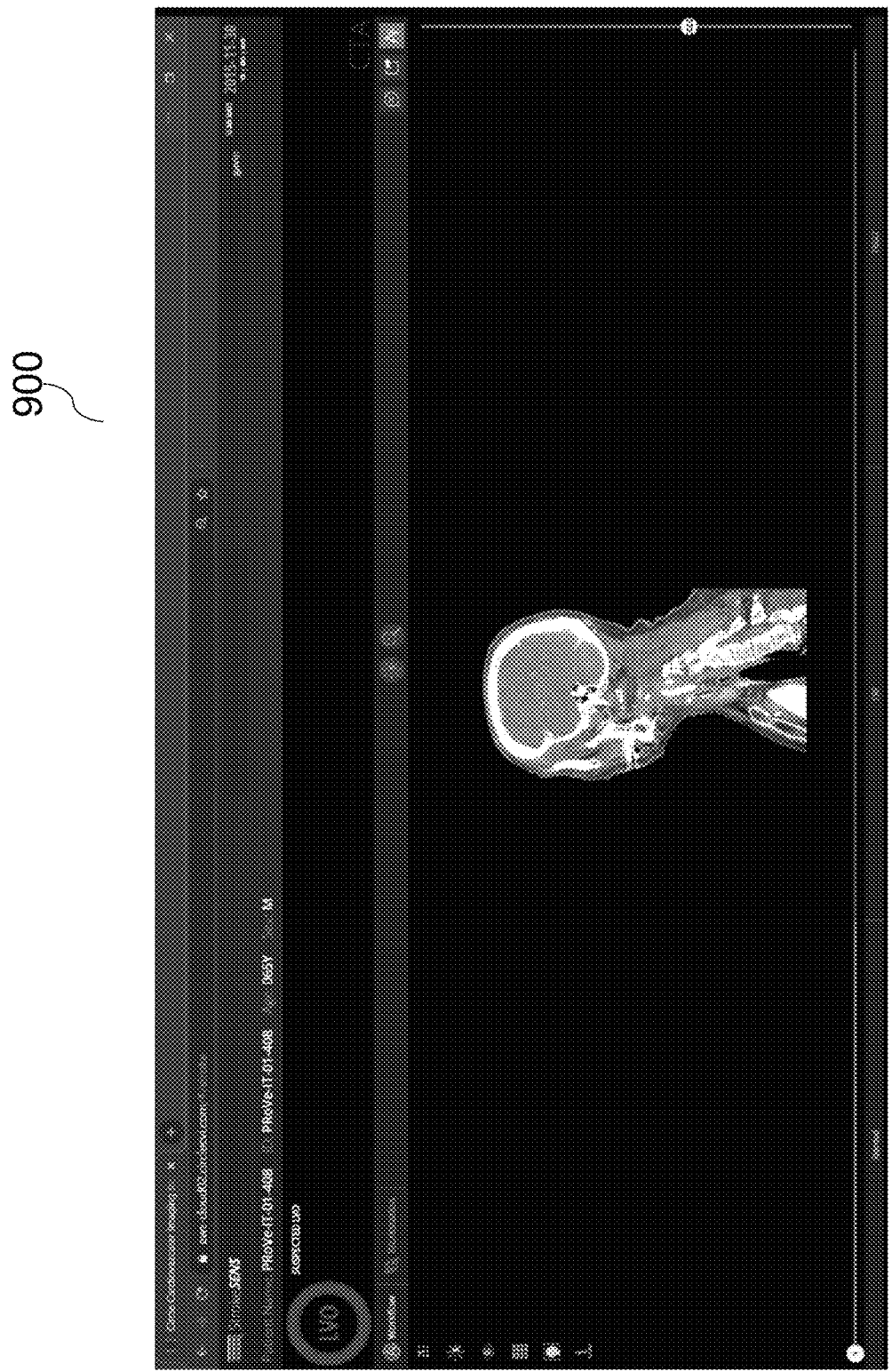
FIG. 9 depicts another screenshot of a graphical user interface (GUI) displaying a medical image on the client-side medical image viewer in accordance with one or more non-limiting embodiments of the present technology.

The client-side medical imaging viewer 257 provides a graphical user interface with one or more viewports for viewing medical images and information related thereto, as well as interface elements such as buttons to interact with viewed medical images, and other functions provided by the medical imaging viewing service 300, which will be explained in more detail herein below. Non-limiting example of a graphical user interface (GUI) 700, 800, 900 showing medical images displayed on the client-side medical imaging viewer 257 in the browser application 255 are illustrated respectively in FIG. 7, FIG. 8 and FIG. 9 in accordance with one or more embodiments of the present technology.

In one or more embodiments, the browser application 255 is configured to use Javascript based image rendering component that use GPU accelerated libraries such as gpu.js and/or low-level graphics API such as webGL for mathematical operations for 3D image rendering purposes including rendering modes like MPR, DVR, surface, etc.

In one or more embodiments, the browser application 255 is configured according to a priority-based proactive caching mechanism that considers user interaction such as movement, speed, and viewer, fetches a window of images the user 252 will most likely view.

Communication Network

In some embodiments of the present technology, the communications network 220 is the Internet. In alternative non-limiting embodiments, the communication network 220 can be implemented as any suitable local area network (LAN), wide area network (WAN), a private communication network or the like. It should be expressly understood that implementations for the communication network 220 are for illustration purposes only. How a communication link 225 (not separately numbered) between the workstation computer 215 and/or the server 230 and/or another electronic device (not illustrated) and the communications network 220 is implemented will depend inter alia on how each of the medical imaging apparatus 210, the workstation computer 215, and the server 230 is implemented.

The communication network 220 may be used in order to transmit data packets amongst one or more of the medical imaging apparatus 210, the workstation computer 215, the server 230, the database 235 and the client device 250. For example, the communication network 220 may be used to transmit requests between the workstation computer 215 and the server 230.

In one or more embodiments, the client device 250 and the server 230 may communicate using the Web Socket communications protocol.

Medical Imaging Viewing Service

Figure 3:
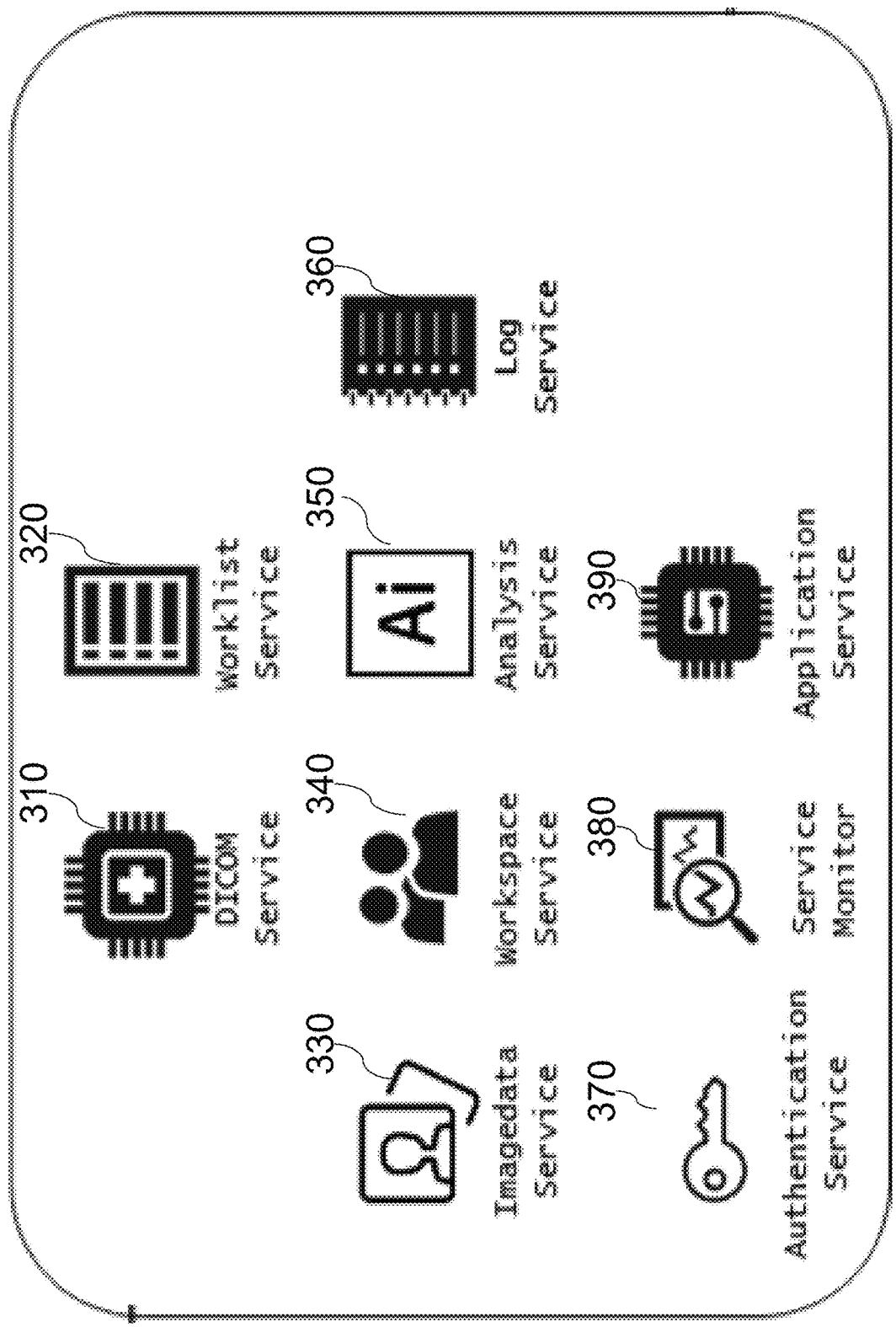
FIG. 3 depicts a schematic diagram of a medical image viewing service in accordance with one or more non-limiting embodiments of the present technology.

Now turning to FIG. 3, there is shown a schematic diagram of a medical imaging viewing service 300, the medical imaging viewing service 300 being implemented in accordance with one or more non-limiting embodiments of the present technology.

In one or more embodiments of the present technology, the server 230 executes the medical imaging viewing service 300. In alternative embodiments, the server 230 may execute at least a portion of the medical imaging viewing service 300, and one or more other servers (not shown) may execute other portions of the medical imaging viewing service 300.

The medical imaging viewing service 300 comprises inter alia a DICOM service 310, a worklist service 320, an image data service 330, a workspace service 340, an analysis service 350, a log service 360, an authentication service 370, a service monitor 380, and an application service 390.

Each of the DICOM service 310, the worklist service 320, the image data service 330, the workspace service 340, the analysis service 350, the log service 360, the authentication service 370, the service monitor 380, and the application service 390 may be executed in a separate virtual machine executed by the server 230.

It will be appreciated that the distinction between the DICOM service 310, the worklist service 320, the image data service 330, the workspace service 340, the analysis service 350, the log service 360, the authentication service 370, the service monitor 380, and the application service 390 are for illustrative purposes only and one or more of the aforementioned services may be combined, omitted and/or implemented in a different manner in accordance with one or more embodiments of the present technology.

DICOM Service

The DICOM service 310 is configured to inter alia: (i) communicate with the medical imaging apparatus 210 and/or the PACS database 217; (ii) receive notifications of images acquired by the medical imaging apparatus 210; (iii) receive images from the PACS database 217; (iv) store the images in the database 235; and (v) transmit an indication of the received data to the worklist service 320.

In one or more embodiments, one or more of the medical imaging apparatus 210, the workstation computer 215, and the PACS database 217 are configured to notify the DICOM service 310 of newly acquired data by the medical imaging apparatus 210. It is contemplated that the acquired data may be automatically transmitted or pushed to the DICOM service 310, or the DICOM service 310 may be first notified of the new images and may acquire the new images upon confirmation.

The DICOM service 310 receives data transmitted by the medical imaging apparatus 210. The DICOM service 310 is configured to accept, identify and store data of the DICOM files in the database 235.

The DICOM service 310 is configured to analyze data related to the images, for example by analyzing the header portion of the transmitted DICOM file. The DICOM service 310 then provides an indication of a new study to the worklist service 320.

Worklist Service

The worklist service 320 is configured to inter alia: (i) receive indications of newly received data from the DICOM service 310; (ii) add the new data pushed to the DICOM service 310 into a worklist or table of contents; and (iii) communicate with the application service 390.

In one or more embodiments, the worklist service 320 lists information relating to the pushed images (e.g. file name), information relating to the medical imaging apparatus 210 (e.g. acquisition parameters, time, etc.), information relating to the patient (e.g. sex, age, conditions), and date. The information may be for example extracted from the header portion of the DICOM files for a given study acquired by the medical imaging apparatus 210.

The worklist service 320 acts a table of content of the medical imaging data pushed to the DICOM service 310.

In one or more embodiments, the worklist service 320 may list, for each user of the medical imaging viewing service 300, if applicable, pending cases, top priority cases, active cases, and completed cases. Each case may be associated with one or more patients. The case list may display information of each authorized case entry including status, patient name, medical condition, and start date. The worklist service 320 may further list detailed information such as written reports from various dates, lab results from various tests and dates, image reports, and medical images that may be displayed and function as a gateway for displaying the listed documents.

Figure 6:
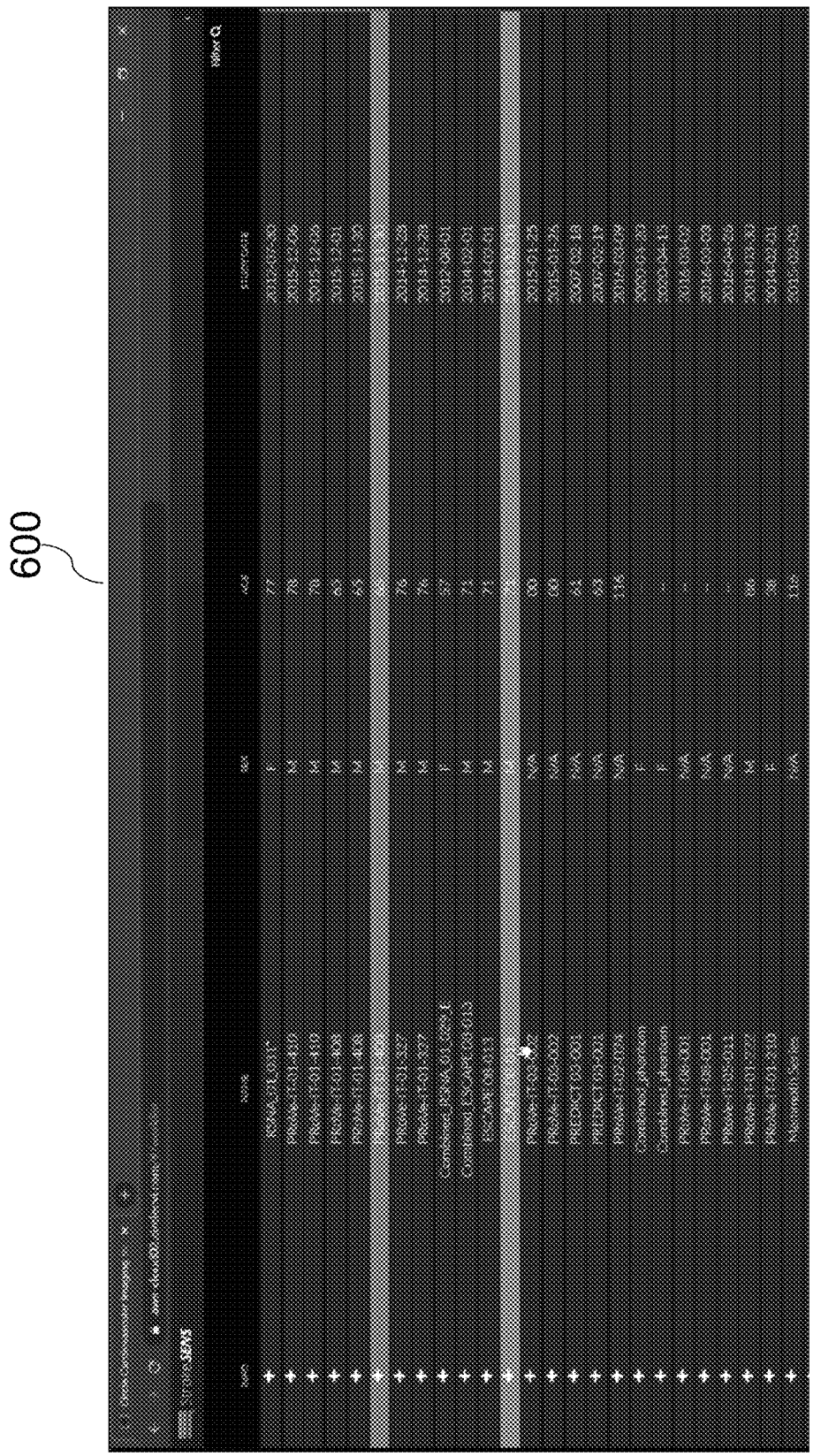
FIG. 6 depicts a screenshot of a worklist displayed on a graphical user interface of a client-side medical image viewer in accordance with one or more non-limiting embodiments of the present technology.

A non-limiting example of a graphical user interface of a worklist 600 displayed on the client-side medical imaging viewer 257 in the browser application 255 and provided by the worklist service 320 displayed to the user 252 is illustrated in FIG. 6.

Imagedata Service

The image data service 330 is configured to inter alia: (i) communicate with the application service 390; (ii) handle requests for 2D and 3D images from client devices such as the client device 250; (iii) perform pixel reading of images in DICOM files to obtain pixel arrays; (iv) perform benchmark testing of client devices such as the client device 250 and the communication network 220; (v) perform just-in-time compression; (vi) perform data marshalling of pixel arrays to obtain binary serialized arrays; (vii) provide hybrid server-side and client-side 2D and 3D image visualization and rendering.

In one or more embodiments, the image data service 330 is configured to provide 2D image visualization including three types of multiplanar sectioning and display, including orthogonal, oblique, and curved planes.

In one or more embodiments, the image data service 330 is configured to provide 3D image visualization including surface renderings and/or volume renderings with projection and surface types. The image data service 330 is configured to perform one or more of: multiplanar reformation (MPR), volume rendering (VR), maximum intensity projection (MIP), minimum intensity projection (MinIP), and surface-shaded display (SSD).

How the image data service 330 is configured to do so will be explained in more detail hereinbelow.

Workspace Service

The workspace service 340 is configured to inter alia: (i) provide image annotation tools for users of the medical imaging viewing service 300; and (ii) store annotations performed by users of the medical imaging viewing service 300 in the database 235.

The annotations tools provided in the graphical user interface are not limited and include annotations tools known in the art. Non-limiting examples of annotation tools include contour drawing tools, labeling tools, and measurement tools.

One or more of the annotation tools may be provided in a portion of the GUI of client-side medical imaging viewer 257 via the browser application 255. The annotation tools may include tools for performing one or more of: fluid zooming and panning, brightness and contrast adjustments, negative mode, pre-set window settings for computed tomography (lung, bone, etc.), ability to rotate (90, 180 degrees) or flip (horizontal and vertical) images, segment length, mean, minimum and maximum parameter values (e.g. density in Hounsfield units in computed tomography) within circle/ellipse and its area, angle value (normal and cobb angle), pen tool for freehand drawing, text box labelling tool, arrows, polygons, and the like.

Analysis Service

The analysis service 350 is configured to inter alia: (i) fetch DICOM images and analyze DICOM images; (ii) store the analysis results in the database 235.

In one or more embodiments, the analysis service 350 is configured to analyze the header portion of DICOM files to extract information therefrom.

The analysis service 350 handles customized image processing and data extraction tasks to provide advanced analysis results for diagnostic assistance and data visualization.

As a non-limiting example, the analysis service 350 may be implemented using C++, Qt, Tensorflow, Python, and ITK.

Log Service

The log service 360 is configured to inter alia: (i) communicate with the DICOM service 310, the worklist service 320, the image data service 330, the workspace service 340, the analysis service 350, the authentication service 370, the service monitor 380, and the application service 390; and (ii) log requests from each of the image data service 330, the workspace service 340, the analysis service 350, the authentication service 370, the service monitor 380, and the application service 390 for debugging and audit trail purposes.

As a non-limiting example, the log service 360 may be implemented using Go, and RabbitMQ. Commercial solutions providing log services include loggly, and SolarWinds.

Authentication Service

The authentication service 370 is configured to inter alia: (i) authenticate users of the medical imaging viewing service 300, such as the user 252 of the client device 250, such that only valid users can access the medical imaging viewing service 300; and (ii) provide functionalities for creating and managing users, groups, and permissions.

In one or more embodiments, the authentication service 370 is implemented in using the Go programming language. Commercial solutions of authentication services include Keycloak, AWS IAM, etc.

Service Monitor

The service monitor 380 is configured to inter alia: (i) communicate with the DICOM service 310, the worklist service 320, the image data service 330, the workspace service 340, the analysis service 350, the log service 360, the authentication service 370, and the application service 390; (ii) monitor available resources for the medical imaging viewing service 300 on the server 230; and (iii) determine availability of the resources for the medical imaging viewing service 300.

In one or more embodiments, the service monitor 380 is configured to monitor the available computational resources and bandwidth resources of the server 230 when performing image analysis and rendering.

The service monitor 380 enables determining the availability of the other services which in turn enables optimization of resources on the server 230 and the client device 250.

In one or more embodiments, the service monitor 380 receives for example information such as number of cases and currently active users on the medical imaging viewing service 300 including related information, the types of rendering of medical images performed, user interactions performed by user(s), CPU and GPU resources used, and the like.

Application Service

The application service 390 is configured to inter alia: (i) communicate with the worklist service 320, the image data service 330, and the service monitor 380; (ii) communicate with client devices connected to the medical imaging viewing service 300, such as the client device 250; (iii) receive requests from the client devices and determine if the image data service 330 is available; (iv) determine if the analysis service 350 needs to start image processing and analysis by communicating with the service monitor 380; and (v) transmit optimized image format to the client device 250 for low latency user interaction.

The application service 390 acts as the business-logic units or manager that coordinates decision-making and information sharing among services within the medical image viewing service 300 upon receiving user requests and scanner updates.

As a non-limiting example, the application service 390 may be implemented using Go, MessagePack, and RabbitMQ.

Automated Analysis Upon Receiving New DICOM

Upon acquiring medical images of a given patient, the medical imaging apparatus 210 and/or the PACS database 217 pushes the study comprising a set of images to the server 230. In one or more embodiments, the study is pushed in the form of a DICOM file comprising a header portion and an imaging data portion.

In one or more embodiments, the DICOM service 310 may store the study or at least a portion of the information extracted therefrom in the database 235.

The worklist service 320 transmits an indication to the application service 390 that a study has been received. The application service 390 transmits an indication to the service monitor 380, which determines if the analysis service 350 must be started for processing the image.

In response, the analysis service 350 starts and fetches image data of the study to start the image analysis. The analysis service 350 then stores the results in the database 235.

User Request for Image Data

The user 252 uses the client device 250 to request display of medical images for a given patient by interacting with the client-side medical imaging viewer 257 in the browser application 255. The browser application 255 transmits the request over the communication network 220 to the server 230.

The application service 390 receives the request from the client device 250 and communicates with the service monitor 380 to verify if the image data service 330 is available. If the image data service 330 is available, the application service 390 triggers the start of the image data service 330.

The image data service 330 starts retrieving images from the DICOM service 310 and transmits the data to the application service 390.

The application service 390 then responds with an optimized lossless image format for transmission to the client device 250, as will be explained below.

Figure 4:
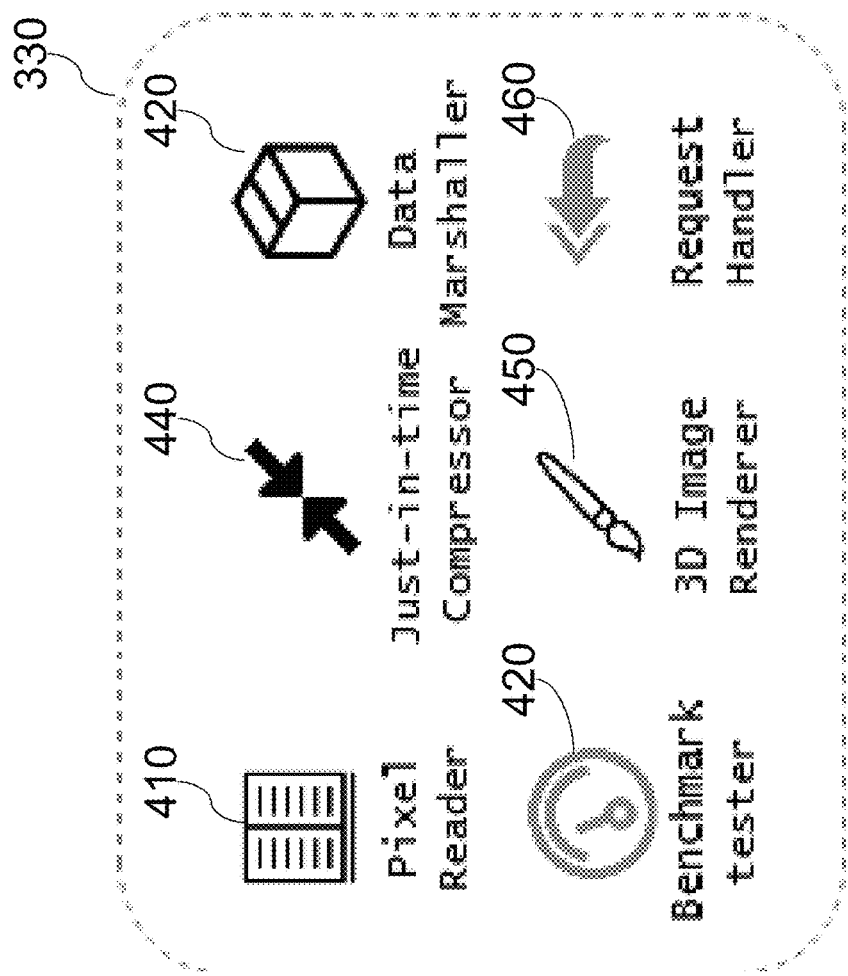
FIG. 4 depicts a schematic diagram of an image data service of the medical imaging viewing service in accordance with one or more non-limiting embodiments of the present technology.

In addition to FIG. 3, reference will now be made to FIG. 4, which illustrates the image data service 330 of the medical imaging viewing service 300 in accordance with one or more non-limiting embodiments of the present technology.

The image data service 330 comprises inter alia pixel reader 410, a data marshaller 420, a benchmark tester 430, a just-in-time compressor 440, and a 3D image renderer 450.

Benchmark Tester

In one or more embodiments, the server 230 uses a benchmark testing routine 430 or benchmark tester 430 to obtain an indication of a performance of one or more of the server 230, the client device 250 and the communication network 220 or the communication link 225. The indication of the benchmark performance may then be used to determine the optimal strategy for compression, processing, transmission and visualization of medical images on the client device 250.

In one or more embodiments, the benchmark tester 430 may perform benchmark testing at predetermined periods of time. It is contemplated that benchmark testing may be performed upon establishing a new session for viewing medical images with a client device such as the client device 250, or upon receiving an indication for processing images in a study, such as 2D and 3D image visualization.

The benchmark tester 430 generates a test data array, the test data array having a size.

The benchmark tester 430 records a first timestamp t1 for the test data array and stores a first timestamp and size of the test data array in the database 235.

The benchmark tester 430 uses a compression algorithm out of a set of compression algorithms to compress the data array and obtain a compressed test array. The compression algorithm for performing the compression may be predetermined or may be chosen randomly.

The benchmark tester 430 records a second timestamp t2 for the compressed test array and stores the second timestamp and a size the compressed test array in the database 235.

The benchmark tester 430 uses the data marshaller 420 to serialize the compressed array and transmits the compressed test array to the browser application 255 of the client device 250.

The browser application 255 receives the compressed data and transmits an indication to the server 230 that the compressed test array has been received.

In one or more embodiments, the browser application 255 decompresses the compressed test array and transmits an indication to the server 230 that the compressed test array has been decompressed.

In one or more embodiments, the browser application 255 may send additional information indicative of the performance of the client device 250 and/or the communication network 220 and communication link 225 together with the indication to the server 230.

The benchmark tester 430 receives the indication from the browser application 255, and records a third timestamp t3.

The benchmark tester 430 determines the transmission speed based on the size of the compressed test array, the third timestamp and the second timestamp.

In one or more embodiments, the benchmark tester 430 determines the transmission speed by calculating: transmissionSpeed=compressedTestArraySize/(t3−t2).

The benchmark tester 430 determines the roundtrip time with compression based on the third timestamp and the first timestamp. In one or more embodiments, the benchmark tester 430 determines the roundtrip time by calculating: t3−t1.

The benchmark tester 430 determines the roundtrip time without compression based on the size of the test data array and the transmission speed. In one or more embodiments, the benchmark tester 430 determines the roundtrip time without compression by calculating: TestArraySize/transmissionSpeed.

The benchmark tester 430 thereby obtains an indication of a performance of the client device 250 and communication network 220 for transmission and processing of medical images. The benchmark tester 430 stores the indication of the performance in the database 235, in association with an indication of the time, the workload of the server 230, the client device 250, and additional information which enables to identify and analyze the performance of the server 230, the client device 250 and the communication link 225 and communication network 220.

In one or more embodiments, the benchmark tester 430 may further test additional aspects of the performance to obtain additional performance information of the client device 250 and the communication network 220 and the communication link 225. In one or more embodiments, the additional performance information of the communication network 220 and the communication link 225 may include measures of packet loss, latency or ping time, and network jitter.

In one or more embodiments, the additional performance information of the server 230 and the client device 250 include scores or measures in CPU tests (e.g. integer, floating and string tests), GPU test (e.g., simulations), drive tests (e.g., read, write, sustained write and mixed I/O), and RAM tests e.g. (single/multi core bandwidth and latency).

It will be appreciated that the benchmark tester 430 may thus test and consider a current performance of one or more of the server 230, the client device 250 and the communication link 225 as well as past performances of the server 230, the client device 250 and the communication link 225.

The indication of the performance provided by the benchmark tester 430 will be used by the image data service 330 to select an optimal strategy for compression and transmission of image data to the client device 250. It will be appreciated that by using the benchmark tester 430, the medical imaging viewing service 300 may determine an optimal strategy such that computational resources and bandwidth are optimized while maximizing user experience when viewing the medical images on the client-side medical imaging viewer 257 via the browser application 255.

Lossless Image Generation

How the medical imaging viewing service 300 generates lossless images for transmission to the client device 250 and display in the client-side medical imaging viewer 257 of the browser application 255 will now be explained.

The image data service 330 receives, via the DICOM service 310, the DICOM file comprising studies for transmission to the client device 250. A study comprises a set of medical images of a patient having been acquired by the medical imaging apparatus 210. In one or more embodiments, the image data service 330 receives the DICOM file from the database 235 or directly from the client device.

The image data service 330 executes a pixel reading routine 410 or pixel reader 410 to generate a data array for each image of the study in the DICOM file. In one or more embodiments, the data array is a pixel data array.

As a non-limiting example, a DICOM ToolKit (DCMTK) may be used to implement the pixel reader 410.

In one or more embodiments, the pixel reader 410 generates a data array for each image in the DICOM file. In one or more other embodiments, the pixel reader 410 may generate a data array for more than one image in the DICOM file. The pixel reader 410 stores the data array in the RAM of the server 230.

In one or more embodiments, the image data service 330 executes the pixel reader 410 on the imaging data portion of the DICOM file. The pixel reader 410 extracts the pixel data from the imaging data portion of the DICOM file and convert the pixel data into a typed representation.

In one or more embodiments, the pixel data comprises RGBA image data.

In one or more embodiments, the typed representation is a base64 format. It will be appreciated that other types of typed representations may be used.

In one or more embodiments, the pixel reader 410 converts the pixel data of each image in the study to a base64 string. The pixel reader 410 then outputs a pixel array.

Just-In-Time Compressor

In one or more embodiments, the image data service 330 is configured to perform dynamic and adaptive compression of the data array by using a just-in-time compressor 440.

The purpose of just-in-time compressor 440 is to select an optimal compression strategy to compress the data array based on the indication of the benchmark performance, i.e. based on one or more of: a transmission speed, a roundtrip time with compression, and a roundtrip time without compression of the client device 250. In one or more embodiments, the optimal compression strategy may include not performing any compression.

The image data service 330 receives the indication of the benchmark performance having been performed by the benchmark tester 430.

In one or more embodiments, the image data service 330 acquires the indication of the benchmark performance associated with the client device 250 from the database 235. In one or more other embodiments, the image data service 330 may use the benchmark tester 430 to obtain the indication of the benchmark performance associated with the client device 250.

In one or more embodiments, the indication of the benchmark performance comprises one or more of: a transmission speed, a roundtrip time with compression, and a roundtrip time without compression. It will be appreciated that the image data service 330 may acquire a plurality of indication of benchmark performances and for example calculate an average benchmark performance. Additionally, the image data service 330 may acquire other information related to the performance of the server 230, the client device 250, the browser application 255, and the communication network 220.

The image data service 330 performs just-in-time compression of the data array based on the indication of the benchmark performance of the client device 250 and the communication network 220. It will be appreciated that the just-in-time compression may be performed for one or more arrays at a time.

In one or more embodiments, the image data service 330 performs just-in-time compression of the data array which is in the form of a pixel array.

The image data service 330 has access to a set of compression algorithms for compressing the data array. The set of compression algorithms comprises one or more compression algorithms.

In one or more embodiments, the set of compression algorithms comprises one or more lossless compression algorithms. It is contemplated that in alternative embodiments of the present technology, the set of compression algorithms may additionally comprise one or more lossy algorithms.

In one or more embodiments, the set of compression algorithms comprises one or more of: LZMA, LZO, DEFLATE, LZ4, ZLIB, zstandard, zip, and bzip2.

In one or more embodiments, each of the compression algorithms is associated with a respective benchmark performance threshold or respective benchmark range. It will be appreciated that there may be a respective benchmark performance threshold or respective benchmark range for each of the transmission speed, the roundtrip time with compression, and the roundtrip time without compression of the client device 250.

Thus, depending on the performance of the client device 250 and the communication link 225, a compression algorithm may be selected dynamically by the image data service 330. The image data service 330 may further take into account factors such as compression time, decompression time and/or compression ratios to select a given compression algorithm in the set.

As a non-limiting example, if the performance of the communication link 225 is deemed to be poor (e.g. below a threshold) but the performance of the client device 214 (e.g. CPU, GPU and memory performance) is deemed to be good (e.g. above a threshold), the image data service 330 may select a first compression algorithm such as zip level 9 to perform compression, which enables a greater compression ratio and which places the burden on the client device 250 to decompress the data.

As another non-limiting example, if the performance of the communication link 225 is deemed to be good (e.g. above a threshold) but the performance of the client device 214 (e.g. CPU, GPU and memory performance) is deemed to be poor (e.g. below a threshold), the image data service 330 may select a second compression algorithm such as zip level 1 to perform compression, which enables a lower compression ratio and which places the burden on the communication link 225.

In one or more embodiments, the benchmark threshold may be determined dynamically. As a non-limiting example, the benchmark threshold may be determined dynamically based on the current workload of the server 230 and/or the client device 250.

In one or more alternative embodiments, the benchmark threshold may be predetermined.

It is contemplated that in one or more alternative embodiments, such as when the benchmark performance is above a threshold, the image data service 330 may not use any compression algorithms.

The just-in-time compressor 440 compresses, using a given one of the set of compression algorithms, the data array to obtain a compressed data array.

In one or more embodiments, the just-in-time compressor 440 compresses, using a given one of the set of compression algorithms, the data array in the form of a pixel array to obtain a compressed pixel array.

In one or more embodiments, the image data service 330 includes an indication of the compression algorithm having been used to compress the data array, which may be used by the client device 250 for performing decompression.

The just-in-time compressor 440 thus enables performing dynamic and adaptive compression of data for transmission to the client device 250 by benchmarking current conditions of one or more of the server 230, the client device 250, and the communication network 220, which improves efficiency of communication.

It will be appreciated that depending on the current available resources, two different compression algorithms (or no compression algorithm at all) may be used to transmit data between the server 230 and the client device 250 at different moments in time.

Data Marshaller

The image data service 330 executes a data marshaller 420 to serialize the data array to obtain a binary serialized array for transmission to the client device 250. In one or more embodiments, the data marshaller 420 serializes the compressed data array to obtain a binary serialized array for transmission to the client device 250.

The data marshaller 420 transforms the memory representation of each data array into a data format suitable for storage and transmission. In one or more embodiments, the data array is in the form of a pixel array. The purpose of the data marshaller 420 is to enable cross language data exchange by performing serialization, thus enabling efficient data transfer between applications by eliminating information redundancy, minimizing latency and size of data transmission of contour measurement by packing complex path data into optimized binary floating-point numeric.

In one or more embodiments, the data marshaller 420 processes the compressed data array or pixel array using MessagePack to obtain a binary serialized array in the form of a msgpack package.

It will be appreciated that msgpack enables to pack the data array or pixel array faster and in a smaller size than by using for example Javascript Object Notation (JSON). The data marshaller 420 may use other types of techniques known in the art to serialize and optimize the pixel array for transmission to the client device 250.

The binary serialized array comprises processed image intensity arrays, image rendering options, annotations, and analytical data of the DICOM file comprising the study or set of images.

The data marshaller 420 outputs the binary serialized array. The data marshaller 420 outputs a binary serialized array for each compressed data array representing an image in a study.

In one or more alternative embodiments, the data marshaller 420 outputs a binary serialized array for more than one image the study.

The binary serialized array is then transmitted to the client device 250. The client device 250 uses the browser application 255 to generate, based on the binary serialized array, the given medical image being represented in the binary serialized array. In one or more embodiments, the browser application 255 deserializer and decompresses the binary serialized array to obtain the original data array.

3D Image Renderer

The 3D image renderer 450 is configured to perform volume-rendering on the server 230 to generate multi-dimensional images or volume for visualization.

The 3D image renderer 450 generates a 3D image based on scene information and camera information. In one or more embodiments, the 3D image renderer 450 receives the scene and camera information from the client device 250. In one or more other embodiments, the 3D image renderer 450 receives the scene and camera information from the database 235 (e.g., when the type of rendering is predetermined).

In one or more embodiments, the 3D image renderer 450 is configured to perform one or more of: multiplanar reformation (MPR), surface rendering (SR), and volume rendering (VR). The 3D image renderer 450 may perform direct rendering and indirect rendering techniques. Direct rendering techniques includes direct volume rendering (DVR) and direct surface rendering (DSR), while indirect rendering includes indirect surface rendering (ISR).

Volume rendering techniques include maximum intensity projection (MIP), curved planar reformation (CPR), ray tracing, surface shaded display (SSD)

DVR techniques generally comprises steps of sampling, classification (assignment of color and opacity) and composing (arrangement of samples classified in 3D volume). DVR comprises techniques such as: ray casting, splatting, shear warp, and texture mapping.

The 3D image renderer 450 is configured to generate, using the pixel arrays, based on the scene and camera information, a 3D image or volume.

The 3D image renderer 450 determines image information needed to generate the 3D image, such as required images, pixels, and performs the 3D image rendering. The 3D image renderer 450 outputs an image corresponding to the requested 3D view.

In one or more embodiments, the 3D image renderer 450 outputs a 2D frame buffer as the rendering result. The 3D image renderer 450 then provides the 2D frame buffer which is transmitted to the client device 250 by using the above-described process with the data marshaller 420 and the just-in-time compressor 440.

The 3D image renderer 450 generates different views of the 3D model based on the scene information and camera setting information, which may be received from the client device 250 upon user interactions being performed (e.g. user performing actions on in the browser application 255 such as rotating, zooming, translating, etc.) with the 2D view of the 3D model.

Thus, the 3D image renderer 450 repeats the 3D rendering and transmits the 2D image showing the 3D visualization upon request in real-time.

Request Handler

The request handler 460 is configured to inter alia: (i) communicate with the pixel reader 410, the data marshaller 420, the benchmark tester 430, the just-in-time compressor 440, and the 3D image renderer 450 (ii) receive requests from services and devices connected to the medical imaging service 300; and (iii) direct the request to the appropriate procedures of the image data service 330 for processing.

Client-Side Processing

The client device 250 receives the compressed binary serialized array from the server 230. In one or more embodiments, each compressed binary serialized array may comprise one or more binary serialized arrays each representing a respective image in the study of the DICOM file.

In one or more alternative embodiments, the client device 250 may receive the binary serialized array, which has not been compressed.

The browser application 255 is configured to implement one or more of Most-Recently-Used (MRU) and Least-Recently-Used (LRU) cache-expiration logic for the storage of the structured binary data to ensure that the storage of the client device 250 is maintained within a reasonable size limit. In one or more embodiments, the browser application 255 is configured according to a priority-based proactive caching mechanism that considers user interaction movement, speed, and viewer, with an algorithm that fetches a window of images the user 252 will most likely view.

In one or more embodiments, the browser application 255 decompresses the compressed binary serialized array to thereby obtain a decompressed serialized binary array. It will be appreciated that the browser application 255 may decompress the compressed binary serialized array based on an indication of the compression algorithm having been used to perform compression by the server 230.

In one or more embodiments, the browser application 255 decodes the decompressed serialized binary array using a client-side data marshaller (not depicted) to obtain the respective pixel array for each respective image in the study, which is stored in the memory cache 259.

In one or more embodiments, the browser application 255 stores each respective pixel array of the study in a HTML tag, which are stored on the client device 250. In one or more embodiments, the browser application 255 converts the binary image into a Base64 format representation, which is converted into an HTML tag and stored in the memory cache 259.

Thus, the client-side medical imaging viewer 257 stores binary data and only converts it to a typed representation when drawing to the HTML5 canvas object, which optimizes memory usage of the browser application 255 and the client device 250.

Upon receiving a request to display a given image, the client-side medical imaging viewer 257 retrieves the pixel array associated with the given image and renders the given image by drawing to the HTML5 canvas object.

It will be appreciated that the request may be received upon a user-interaction performed by the user 252 on the client-side medical imaging viewer 257. As a non-limiting example, the user 252 may navigate to a specific slice or image of the study in the GUI of the client-side medical imaging viewer 257.

When a viewport or a rendering component of the client-side medical imaging viewer 257 requests data for rendering in the browser application 255 (for example, in response to a user interaction of the user 252), the browser application 255 first looks up the stored data in the memory cache 259.

The browser application 255 begins rendering the given image of the study based on the respective pixel array if present in the memory cache 259. In one or more embodiments, the respective pixel array comprises analytical data (e.g. annotations) that are rendered together with the given image.

In one or more embodiments, the browser application 255 uses the HTML5 canvas element to reconstruct the given image pixel-by-pixel based on the respective pixel array. In one or more embodiments, the pixel array is inflated and cast to a typed array to reconstruct an RGBA image data that is rendered with the HTML5 canvas.

The browser application 255 displays the given image to the user 252 of the client device 250 on the user interface of the client-side medical imaging viewer 257.

User Interactions

The user 252 then interacts with the study on the user interface of the client-side medical imaging viewer 257 by performing one or more user interactions via an input/output device (e.g. mouse, keyboard, touch device) of the client device 250.

The user interactions may include viewing a specific image or slice, performing 2D image processing functions such as windowing, panning, magnification or zooming, rotating, flipping, filtering, thresholding, edge detection, etc.

The browser application 255 is configured to perform windowing by calculating the user 252's horizontal and vertical movements in the viewer and dynamically adjust the window width and window center in real time. The pixel data is recalculated based on the new window width and window center values in real-time to allow for dynamic windowing.

The browser application 255 is configured to perform zooming by measuring the user 252's horizontal and vertical movements in the viewer and dynamically changing the canvas zoom, width, and height to allow real-time dynamic zoom interaction with the images.

The browser application 255 is configured to render image(s), overlays, and contours separate canvas elements overlaid on top of each other. Cascade styling sheet (CSS) is used to control the zooming, visibility, pointer interactions, and styling of each canvas in the viewer.

The user interactions may also include requesting 3D visualization of the study, and related 3D processing functions.

In one or more embodiments, the user interactions may include viewing and comparing multiple sequences next to each other, viewing and comparing multiple scans of one patient next to each other, and the like.

The user interactions may include annotations the image using an annotation tool (e.g., label, measure, segment, comment, draw a polygon, color, etc.).

The browser application 255 is configured to track and store each user interaction on the client device 250 and transmit the user interactions performed by the user 252 to the server 230. Each user interaction may be stored in the database 235 with an indication of the user 252, the type of study viewed, type of medical imaging apparatus, patient, condition, a timestamp, and additional statistics related to the user 252 or the client device 250.

In one or more embodiments, the database 235 stores user interaction data for each user of the medical imaging viewing service 300.

The user interactions of the user 252 may be further analyzed by the server 230 and used to predict actions of the user 252 or users of the medical image viewing service 300 in general, which will enable to preload and cache certain images.

In one or more embodiments, the medical imaging viewing service 300 is configured to transmit data not having been explicitly requested by the client device 250. The medical imaging viewing service 300 may for example predict potential request based on past requests for images views, the user 252 and other users' past user interactions including idle time, requested type of 2D and 3D views, and transfer the data to the client device 250. Thus, when the user 252 requests to view a specific image (e.g. slice), or perform a certain action, the requested action may already be present in the memory cache 259 and may be directly rendered by the browser application 255, thus minimizing delay and improving user experience.

Responsive Slice Navigation

Figure 5:
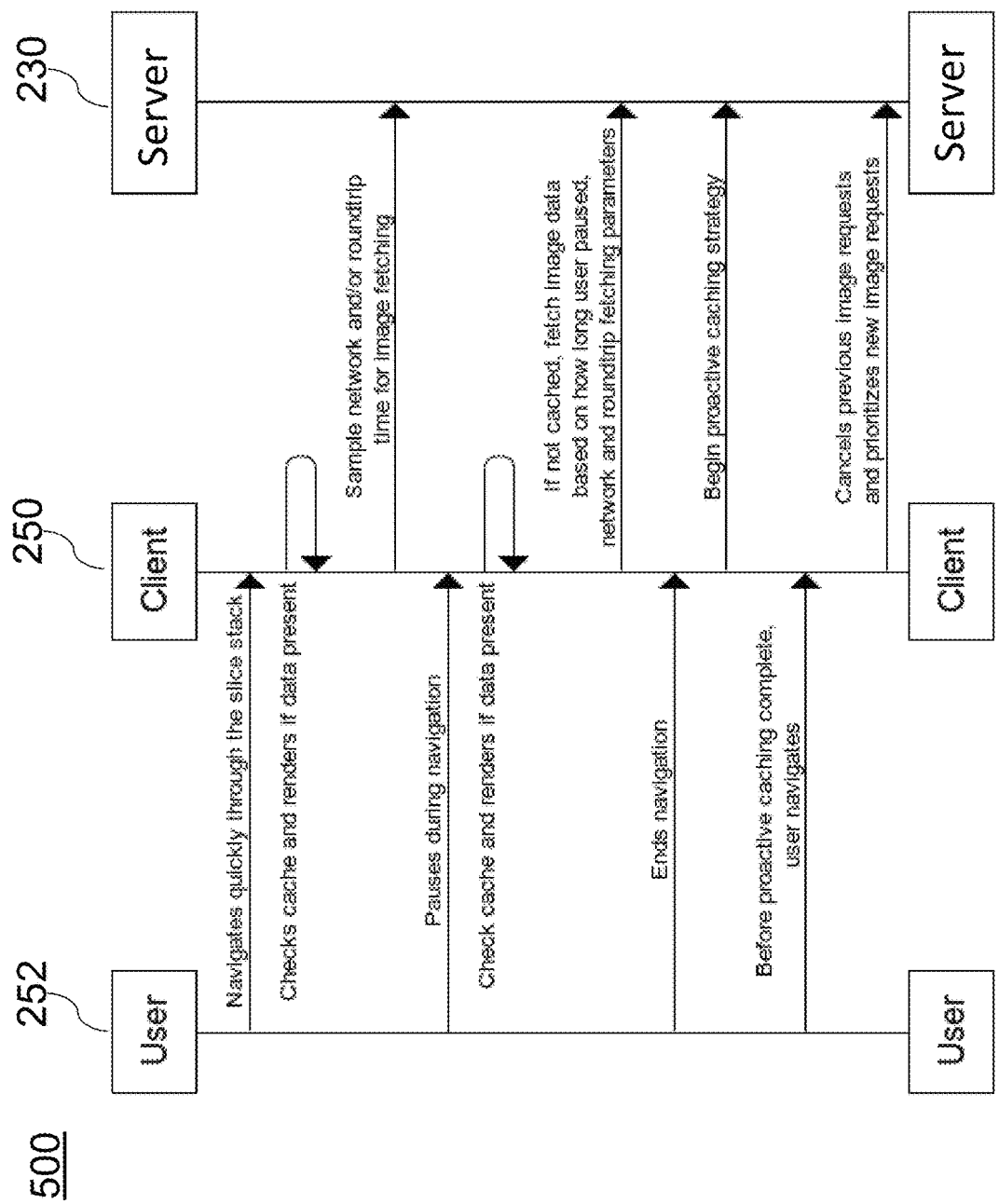
FIG. 5 depicts a communication flow of responsive slice navigation of medical images within the medical image viewing service in accordance with one or more non-limiting embodiments of the present technology.

With reference to FIG. 5, a non-limiting example of how responsive slice navigation 500 may be performed by the user 252 will now be described.

The user 252 may navigate through the slice stack of the study on the client-side medical imaging viewer 257. In response, the browser application 255 may verify if data for rendering the slices is present in the memory cache 259 and if present, the browser application 255 renders the requested slice(s) on the user interface of the client-side medical imaging viewer 257. Additionally, the browser application 255 may perform benchmark testing to determine parameters required for image fetching.

The user 252 may pause during navigation of the slices in the study, for example to view and analyze a specific slice. The browser application 255 tracks the time during which the user 252 pauses. In response, the browser application 255 may verify if data for rendering additional slices is present in the memory cache 259 and if present, the browser application 255 renders the additional slice(s) on the user interface of the client-side medical imaging viewer 257.

If data for rendering the additional slices is not present in the memory cache 259, the browser application 255 fetches the required data based on the pause time, as well as the indication of the benchmark performance. The browser application 255 renders the additional slice(s) on the user interface of the client-side medical imaging viewer 257.

In one or more embodiments, based on past user interactions, the client-side medical imaging viewer 257 may for example request, from the server 230, data for rendering additional slices within a predetermined range of the currently displayed slice without explicitly receiving a request from the user 252, so as to minimize delay for the user 252 if he explicitly requests the slices.

As a non-limiting example, the server 230 may provide the user with the next 10 slices and/or the 10 previous slices without having received a request from the client device 250, because the server 230 has determined based on past user interaction data that these correspond to most actions user(s) after viewing the current slice. As another non-limiting example, for medical images of a given patient already having been viewed by the user 252 at different times (e.g. in follow-up scans), the server 230 may transmit the images in the study which correspond to image already having been viewed by the user 252 (e.g. images which correspond to a region of interest to the user 252).

The user 252 may end the navigation and interactions with the slices of the study. In one or more alternative embodiments, the browser application 255 is configured to begin proactive caching strategy for the study by transmitting a request to the server 230.

In one or more embodiments, while proactive caching is performed, the user 252 may navigate to a different type of view or different study. In such instances, the proactive caching may be interrupted, and the browser application 255 prioritizes the new image requests.

As stated hereinabove, the browser application 255 is configured to log each user interaction in a local database (not depicted), and transmit the user interactions to the medical imaging viewing service 300.

Real-Time 2D Image Visualization

In one or more embodiments, the user 252 may request a 2D image visualization different from the one that is currently displayed by the client-side medical imaging viewer 257. In one or more embodiments, the 2D image visualization may include three types of multiplanar sectioning and display, including orthogonal, oblique, and curved planes For example, an axial view of a body of a subject may be displayed to the user 252 on the user interface of the client-side medical imaging viewer 257 and the user 252 may wish to display a coronal view, a sagittal-right or a sagittal-left view of the study.

In one or more embodiments, the client-side medical imaging viewer 257 is configured to perform multiplanar reformation or reconstruction (MPR) to reformat imaging data. The client-side medical imaging viewer 257 may be configured to perform maximum intensity projections (MIPs) and/or minimum intensity projections (MinIPs).

In one or more embodiments, the medical imaging viewing service 300 is configured to transmit, to the browser application 255, data required for generating the requested 2D view.

The browser application 255 receives the data required for generating the 2D view for display on the client-side medical imaging viewer 257. In one or more embodiments, the browser application 255 decompresses the data and unmarshalls the data to obtain the pixel array. The browser application 255 applies windowing according to the image parameters, and uses the HTML canvas drawimage API to draw the image in the canvas from the pixel array.

In one or more embodiments, the server 230 is configured to predict, based on past user interaction data, images that will be viewed by the user 252. The predictions may be based on past user interactions of the user 252, past user interactions of other users of the medical imaging viewing service 300 and considering factors such as type of medical imaging apparatus 210, acquisition parameters, patient information, similar images having been seen by user 252 or other users and/or past images of the same patient. The server 230 predicts which images of a study will be viewed and will provide the client side 250 with the predicted images without an explicit request from the client device 250. The predicted images may be stored in a volatile memory of the client device 250 (e.g. memory cache 259 or RAM) upon being requested for viewing by the user 252.

In one or more embodiments, the server 230 has access to different types of machine learning models trained to perform predictions based on past user interaction data.

Hybrid Real-Time Multi-Dimensional Image Visualization

In one or more embodiments, the user 252 may request to perform multi-dimensional image visualization of the study on the GUI of the client-side medical imaging viewer 257.

The medical imaging viewing service 300 uses the 3D image renderer 450 to perform multi-dimensional image visualization. It will be appreciated that multi-dimensional visualization may include 3D and 4D image visualization and may include surface rendering and/or volume renderings (projection and surface types) techniques. The type of multi-dimensional image visualization provided depends inter alia on the type of images in the study, components of the server 230 and client devices, as well as the specific rendering techniques implemented within the communication system 200.

The user 252 may request to perform 3D image visualization of the study on the user interface of the client-side medical imaging viewer 257 by performing a user-interaction, e.g. by clicking or selecting a user interface element such as a button. The user-interaction causes a request to be transmitted from the client device 250 to the server 230.

The image data service 330 of the server 230 receives the request for a 3D visualization of the 3D image. In one or more embodiments, the request comprises a type of 3D visualization to generate and includes information about a scene and camera setting.

The image data service 330 retrieves the data required to generate the 3D image by the client device 250. In one or more embodiments, the image data service 330 retrieves images in the study required to generate the 3D visualization from the database 235 based on the requested 3D view, which includes information about the scene and camera settings. It will be appreciated that at least a portion of the images required to generate the 3D visualization requested by the user 252 may not have been yet transmitted to the client device 250.

In one or more embodiments, upon receiving a request for 3D visualization of a study, the medical imaging viewing service 300 is configured to determine an optimal strategy for generating the 3D visualization. The medical imaging viewing service 300 is configured to determine a performance of server 230 and the client device 250, as well as a performance of the communication link 225.

In one or more embodiments, the medical imaging viewing service 300 uses the benchmark tester 430 to determine a performance of the server 230, the client device 250, and the communication link 225 for performing 3D visualization. The benchmark tester 430 may for example acquire performance information of the server 230 and the client device 250 specifically related to 3D rendering, to determine for example whether the client device 250 has sufficiently powerful components (CPU, GPU, RAM, etc.) and available resources to perform the required rendering for generating the 3D visualization, as well as the if the server 230 has enough currently available resources to generate the 3D rendering (e.g., if the medical imaging viewing service 300 is busy performing 3D rendering or for other users of the service, it may not be available to perform the rendering). The benchmark tester 430 may consider the currently available resources and/or past available resources of the server 230, the client device 250, and the communication link 225.

The image data service 330 transmits, to the client device 250, the data required to render the 3D image or volume. It will be appreciated that the data may include for example thousands of pixel arrays representing medical images which may be processed by the client device 250 to obtain the 3D visualization.

In one or more embodiments, the image data service 330 may determine to transmit the images for 3D rendering on the client device 250 based on the indication of the performance of the client device 250, and the communication link 225 with the server 230. Such may be the case when the client device 250 has a performance satisfactory (e.g. above a threshold) and can perform the rendering of the 3D images and/or when the server 230 does not have additional resources available for rendering the 3D image.

The client-side medical imaging viewer 257 receives, from the server 230, images required for building the 3D model requested by the user 252. It will be appreciated that the images may be converted into a data or pixel array, binarized and serialized and compressed (if necessary) before being transmitted to the client device 250, as previously described. The binary serialized arrays are transmitted sequentially.

As a non-limiting example, for the maximum intensity projection (MIP) rendering of an axial sliced CT image volume, the volume is first divided to a plurality of slabs. Within each slab, the browser application 255 calculates the MIP and caches the MIP within the memory cache 259. When the user 252 interacts with the volume, e.g., navigates through the slice locations, cached MIP images of slabs are used to speed up the computation process.

The server 230 and/or the client device 250 tracks the time taken to transmit the images as well as the download speed and connection performance during transmission.

If the time taken to transmit the required image data for rendering the 3D visualization as well as the download speed and/or connection performance is below a threshold, the image data service 330 may determine to perform real-time 3D rendering of the images on the server 230 by using the 3D image renderer 450, and transmit the rendered image data to the client-side medical imaging viewer 257 for viewing, and may then resume the transmission of the required image data for rendering the requested 3D visualization by the client device 250. In one or more embodiments, the client device 250 may be powerful enough (e.g. indication of performance and/or available resources above a threshold) to perform the rendering of the images for generating the 3D visualization requested by the user 252, but it may be determined that the transmission of the data required to perform the visualization is too slow (e.g. performance of the connection and/or download speed below a threshold), which results in a detrimental user experience during which the user 252 does not have access to the requested 3D visualization because all the data required for generating the 3D visualization has not yet been received by the client device 250. In such instances, the image data service 330 may generate the requested 3D visualization and pause the transmission of the image data required to perform the 3D visualization rendering on the client device 250, transmit the image data corresponding to the rendered 3D visualization (e.g. 2D frame buffer), which enables the user 252 to view the rendered 3D view, while the transmission of the image data continues until the client device 252 has the required imaging data to generate the 3D visualization.

Additionally or alternatively, the image data service 330 also takes into account the indication of the performance of the client device 250 and/or the communication link 225 to determine whether to perform real-time 3D rendering of the images on the server side. If it is determined that the performance of the client device 250 and/or the communication link 225 is below a threshold, the rendering of the 3D visualization may be performed on the server 230 and the rendered image data (e.g., 2D frame buffers) may be transmitted to the client device 250. In other words, the server 230 may "stream" the 3D rendering of the images if it is determined that the required image data to process the 3D images will be too slow or the client device 250 does not have sufficient available resources or a sufficient performance to render, thus enabling the user 252 to appreciate and interact with the requested 3D visualization in lower quality.

Method Description

Figure 10:
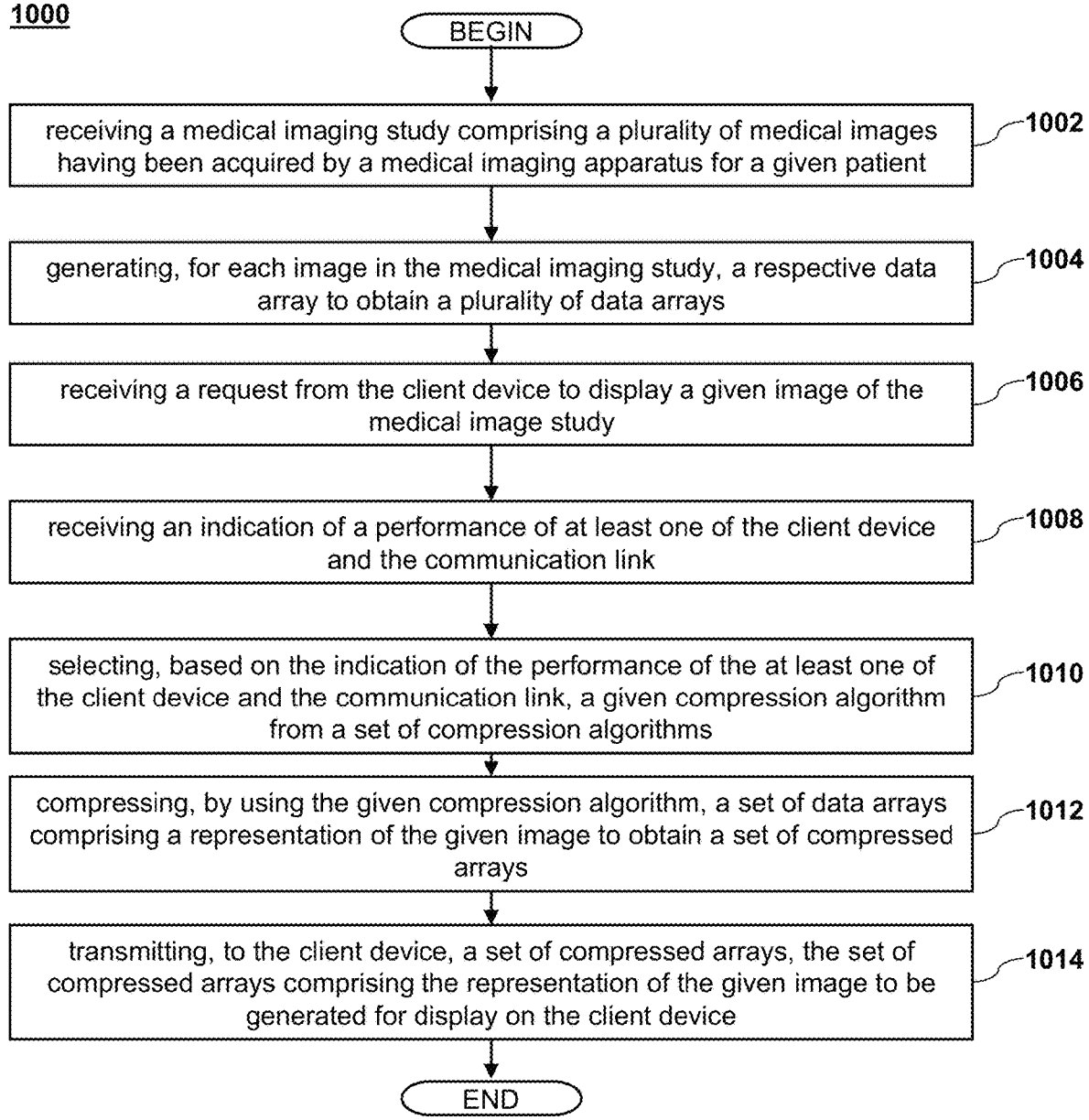
FIG. 10 depicts a flow chart of a method for web-based medical image processing in accordance with one or more non-limiting embodiments of the present technology.

FIG. 10 depicts a flowchart of a method 1000 for web-based medical image processing in accordance with one or more non-limiting embodiments of the present technology.

The method 1000 is executed within the system 200.

In one or more embodiments, the server 230 comprises a processing device such as the processor 110 and/or the GPU 111 operatively connected to a non-transitory computer readable storage medium such as the solid-state drive 120 and/or the random-access memory 130 storing computer-readable instructions. The processing device, upon executing the computer-readable instructions, is configured to or operable to execute the method 1000.

The method 1000 begins at processing step 1002.

At processing step 1002, the server 230 receives a medical imaging study comprising a plurality of medical images having been acquired by a medical imaging apparatus for a given patient.

In one or more embodiments, the medical imaging study comprising the plurality of medical images is in a DICOM format comprising a header portion and an imaging portion.

At processing step 1004, the server 230 generates for each image in the medical imaging study, a respective data array to obtain a plurality of data arrays.

In one or more embodiments, the server 230 generates the respective data array in the form of a respective pixel array using the pixel reader 410.

At processing step 1006, the server 230 receives, from the client device 250, a request to display a given image of the medical image study.

In one or more embodiments, prior to step 1006, the server 230 transmits an indication that the study is available to user 252 of the client device 250.

As a non-limiting example, the request to display a given image of the medical image study may be a request to display a specific slice of the study stack.

At processing step 1008, the server 230 performs benchmark testing with the client device 250 to obtain an indication of a performance of at least one of the client device and the communication link.

In one or more embodiments, the server 230 uses the benchmark tester 430 to perform the benchmark testing and obtain the indication of the performance.

In one or more embodiments, the server 230 generates a test array, the test array having a first size and being associated with a first timestamp, and compresses, using one of the set of compression algorithms, the test array to obtain a compressed test array, the compressed test array having a second size being associated with a second timestamp.

The server 230 transmits to the client device 250, the compressed test array, and receives, from the client device 250, an indication of a decompressed test data array, the indication of the test data array being associated with a third timestamp.

The server 230 then determines, based on the first timestamp, the second timestamp, the third timestamp, the first size and the second size, the indication of the performance of the at least one of the client device 250 and the communication link 225.

In one or more embodiments, the server 230 determines: (i) a transmission speed based on the second size, the third timestamp and the second timestamp; (ii) a compressed roundtrip time based on the third timestamp and the first timestamp; and (iii) an uncompressed roundtrip time based on the first size, the third timestamp and the first timestamp.

At processing step 1010, the server 230 selects, based on the indication of the performance of the at least one of the client device 250 and the communication link 225, a given compression algorithm from a set of compression algorithms.

In one or more embodiments, the server 230 selects the given compression algorithm based on the indication of the performance of the at least one of the client device 250 and the communication link 225 being above a threshold.

At processing step 1012, the server 230 compresses, by using the given compression algorithm, a set of data arrays to obtain a set of compressed arrays. The set of compressed arrays comprises at least a representation of the given image requested by the client device 250.

In one or more embodiments, the server 230 determines or predicts, based on past user interaction data stored in the database 235, at least one other image that may be requested by the client device 230 but which has not been explicitly requested by the client device 250. The server 230 selects the set of data arrays from the plurality of data arrays, the set of data arrays comprising a representation of: the given image requested by the client device 250 and the at least one other image not having been explicitly requested by the client device 250. The server 230 then compresses the set of data arrays by using the given compression algorithm to obtain the set of compressed data arrays.

In one or more embodiments, the server 230 uses the just-in-time compressor 440 to perform the compression by using the given compression algorithm.

In one or more embodiments, the server 230 uses the data marshaller 420 to serialize the set of compressed arrays to obtain a set of binary serialized compressed arrays for transmission to the client device 250.

At processing step 1014, the server 230 transmits to the client device 250, the set of compressed arrays, the set of compressed arrays comprising a representation of the given image to be generated for display on the client device 250.

The client device 250 is configured to unmarshall and decompress the set of compressed data arrays, and generate, using the data array representing the given image, the given image for display on a user interface of the browser application 255.

The method 1000 then ends.

Figure 11:
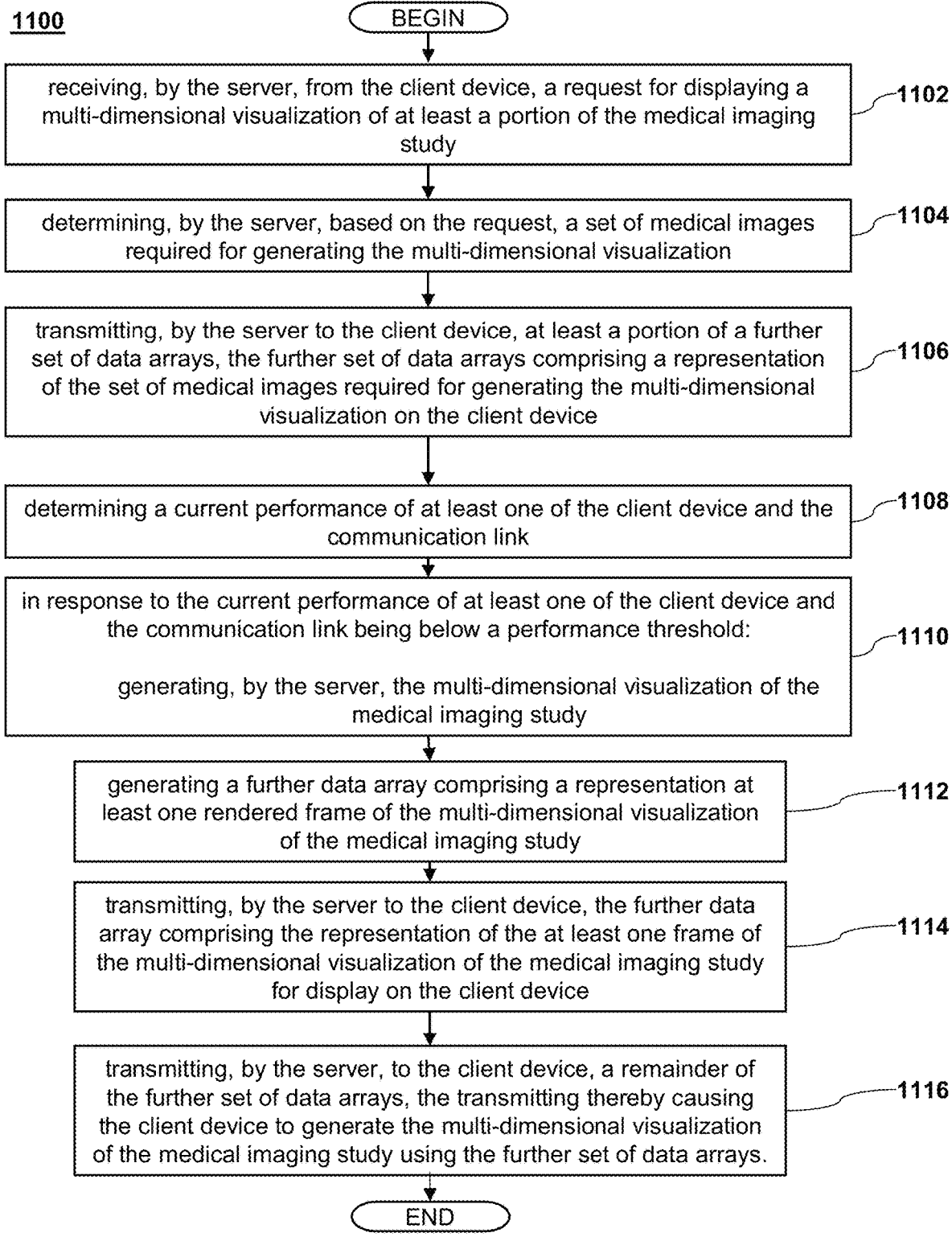
FIG. 11 depicts a flow chart of a method for web-based multi-dimensional medical image rendering in accordance with one or more non-limiting embodiments of the present technology.

FIG. 11 depicts a flowchart of a method 1100 for web-based multi-dimensional medical image rendering in accordance with one or more non-limiting embodiments of the present technology.

The method 1100 is executed within the system 200. The method 1100 may be executed after the method 1000.

In one or more embodiments, the server 230 comprises a processing device such as the processor 110 and/or the GPU 111 operatively connected to a non-transitory computer readable storage medium such as the solid-state drive 120 and/or the random-access memory 130 storing computer-readable instructions. The processing device, upon executing the computer-readable instructions, is configured to or operable to execute the method 1100.

The method 1100 begins at processing step 1002.

At processing step 1102, the server 230 receives, from the client device 250, a request for displaying a multi-dimensional visualization of at least a portion of the medical imaging study.

In one or more embodiments, the request comprises a scene information and a camera setting of the multi-dimensional visualization.

At processing step 1104, the server 230 determines, based on the request, a set of medical images required for generating the multi-dimensional visualization.

In one or more embodiments, the server 230 determines the set of medical images required for generating or rendering the multi-dimensional visualization from the plurality of medical images of the medical imaging study. In one or more embodiments, the server 230 determines the set of medical images required for generating or rendering the multi-dimensional visualization based on the scene information and the camera setting.

At processing step 1106, the server 230 transmits, to the client device 250, at least a portion of a further set of data arrays, the further set of data arrays comprising a representation of the set of medical images required for generating the multi-dimensional visualization on the client device;

At processing step 1108, the server 230 determines a current performance of at least one of the client device 250 and the communication link 225 during transmission of the further set of data arrays.

In one or more embodiments, the server 230 determines currently available resources of the client device 250 and a current performance of the communication link 225. The current performance of the communication link 225 includes a transmission speed.

At processing step 1110, in response to the current performance of at least one of the client device and the communication link being below a performance threshold: the server 230 generates the multi-dimensional visualization of the medical imaging study.

In one or more embodiments, the server 230 uses the 3D image renderer 450 to generate the requested multi-dimensional visualization of the medical imaging study. In one or more embodiments, the server 230 In one or more embodiments, the server 230 is configured to perform one or more of: multiplanar reformation (MPR), surface rendering (SR), and volume rendering (VR). In one or more embodiments, the server 230 is configured to perform direct rendering and indirect rendering techniques. Direct rendering techniques includes direct volume rendering (DVR) and direct surface rendering (DSR), while indirect rendering includes indirect surface rendering (ISR).

At processing step 1112, the server 230 generates a further data array comprising a representation at least one frame of the multi-dimensional visualization of the medical imaging study. In one or more embodiments, the server 230 generates a 2D frame buffer of the requested multi-dimensional visualization.

At processing step 1114, the server 230 transmits, to the client device 250, the further data array comprising the representation of the at least one rendered frame of the multi-dimensional visualization of the medical imaging study for display on the client device 250. The client device 250 can thus display the multi-dimensional rendering while the remainder of the required further set of data array is being transmitted to the client device At processing step 1116, the server 230 transmits to the client device 250 a remainder of the further set of data arrays, the transmitting thereby causing the client device to generate the multi-dimensional visualization of the medical imaging study using the further set of data arrays.

One or more embodiments of the present technology provide a web-based client that uses adaptive debouncing and caching mechanisms which enables fetching and rendering data with minimal delays and which provides real-time user experience.

One or more embodiments of the present technology provide a web-based client using a customized volumetric image rendering algorithm which enables performing intensity projection renderings, for example maximum intensity projection by optimizing memory and CPU usage.

One or more embodiments of the present technology provide a web-client that stores binary data and only converts it to a typed representation when drawing to the HTML5 Canvas object, which optimizes browser memory usages.

One or more embodiments of the present technology provide a web-client using a priority-based proactive caching mechanism that considers user interaction movement, speed, and viewer, with an algorithm that fetches a window of images the user will most likely view.

One or more embodiments of the present technology provide a system which uses a customized binary data structure for transferring image and post-processing data between the server and the web-based client, which in turn enables optimizing network bandwidth usages and data packing/unpacking.

One or more embodiments of the present technology provide a system that uses bi-directional communication which enables a server to push data or messages voluntarily to the web-based client to streamline client image analysis workflow, based on the server-side user behavior prediction and analysis.

One or more embodiments of the present technology provide a system that uses adaptively configurable data compression by proactively benchmarking network/server conditions to further improve the efficiency of communications.

One or more embodiments of the present technology provide a system using multi-threaded operations to request and fetch data without blocking the main UI thread, which allows better user experience.

One or more embodiments of the present technology provide a complete software system with components above and additional image processing services allowing multiple physicians to work collaboratively via the software.

One or more embodiments of the present technology provide a high-performance software system with components above allowing a variety of medical image post-processing and clinical analysis workflows.

It should be expressly understood that not all technical effects mentioned herein need to be enjoyed in each and every embodiment of the present technology. For example, embodiments of the present technology may be implemented without the user enjoying some of these technical effects, while other non-limiting embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fiber-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

What is claimed is:

1. A method for displaying a medical image on a client device connected to a server via communication link over communication network, the method comprising:
    receiving, by the server, a medical imaging study comprising a plurality of medical images having been acquired by a medical imaging apparatus for a given patient;
    generating, by the server, for each image of the plurality of images in the medical imaging study, a respective data array to obtain a plurality of data arrays;
    receiving, by the server from the client device, a request to display a given image of the medical image study;
    performing benchmark testing with the client device to obtain an indication of a performance of at least one of the client device and the communication link, wherein the performing the benchmark testing with the client device comprises:
        generating, by the server, a test array, the test array having a first size and being associated with a first timestamp;
        compressing, by the server, using one of the set of compression algorithms, the test array to obtain a compressed test array, the compressed test array having a second size being associated with a second timestamp;
        transmitting, by the server to the client device, the compressed test array;
        receiving, by the server from the client device, an indication of a decompressed test data array, the indication of the test data array being associated with a third timestamp; and
        determining, based on the first timestamp, the second timestamp, the third timestamp, the first size and the second size, the indication of the performance of the at least one of the client device and the communication link;
    selecting, based on the indication of the performance of the at least one of the client device and the communication link, a given compression algorithm from a set of compression algorithms;
    compressing, by using the given compression algorithm, a set of data arrays comprising a representation of the given image to obtain a set of compressed arrays; and
    transmitting, to the client device, the set of compressed arrays, the set of compressed arrays comprising the representation of the given image to be generated for display on the client device.

2. The method of claim 1, wherein the determining the indication of the performance of the at least one of the client device and the communication link comprises:
- determining a transmission speed based on the second size, the third timestamp and the second timestamp;
- determining a compressed roundtrip time based on the third timestamp and the first timestamp; and
- determining an uncompressed roundtrip time based on the first size, the third timestamp and the first timestamp.

3. The method of claim 1, further comprising, prior to said transmitting, to the client device, the set of compressed array comprising the representation of the given image:
- receiving past user interaction data from a database connected to the server; and
- selecting, based on the past user interaction data, the set of compressed arrays from the plurality of compressed arrays, the set of compressed arrays comprising a representation of at least one other image not having been explicitly requested by the client device.

4. The method of claim 3, wherein the past user interaction data comprises at least one of: past user interaction data of a user of the client device, past interaction data related to the given patient, and past interaction data related to similar medical imaging studies having been previously interacted with.

5. The method of claim 1, further comprising:
- receiving, by the server, from the client device, a request for displaying a multi-dimensional visualization of at least a portion of the medical imaging study;
- determining, by the server, based on the request, a set of medical images required for generating the multi-dimensional visualization;
- transmitting, by the server to the client device, at least a portion of a further set of data arrays, the further set of data arrays comprising a representation of the set of medical images required for generating the multi-dimensional visualization on the client device;
- determining a current performance of at least one of the client device and the communication link; and
- in response to the current performance of at least one of the client device and the communication link being below a performance threshold:
  - generating, by the server, the multi-dimensional visualization of the medical imaging study;
  - generating a further data array comprising a representation at least one rendered frame of the multi-dimensional visualization of the medical imaging study; and
  - transmitting, by the server to the client device, the further data array comprising the representation of the at least one frame of the multi-dimensional visualization of the medical imaging study for display on the client device.

6. The method of claim 5, further comprising:
- transmitting, by the server, to the client device, a remainder of the further set of data arrays, the transmitting thereby causing the client device to generate the multi-dimensional visualization of the medical imaging study using the further set of data arrays.

7. The method of claim 6, wherein the request for displaying the multi-dimensional visualization of the medical imaging study comprises a scene information and a camera setting; and wherein said determining the set of medical images required for generating the multi-dimensional visualization is based on the scene information and the camera setting.

8. The method of claim 5, wherein said transmitting, by the server to the client device, at least the portion of the further set of data arrays comprises: compressing, by using the given compression algorithm, at least the portion of the further set of data arrays to obtain compressed further data arrays.

9. The method of claim 5, wherein said determining a current performance of at least one of the client device and the communication link respectively comprises: determining available computational resources on the client device, determining a transmission time, and determining a transmission speed.

10. The method of claim 1, wherein said transmitting, to the client device, the set of compressed arrays comprises marshalling the set of compressed arrays to obtain a set of binary serialized compressed arrays and transmitting the set of binary serialized compressed arrays to the client device.

11. A system comprising:
- a processor; and
- a non-transitory storage medium operatively connected to the processor, the non-transitory storage medium storing computer-readable instructions thereon;
- the system being connected to a client device via a communication link over a communication network,
- the processor, upon executing the computer-readable instructions, being configured for:
  - receiving a medical imaging study comprising a plurality of medical images having been acquired by a medical imaging apparatus for a given patient;
  - generating for each image of the plurality of images in the medical imaging study, a respective data array to obtain a plurality of data arrays;
  - receiving, from the client device, a request to display a given image of the medical image study;
  - performing benchmark testing with the client device to obtain an indication of a performance of at least one of the client device and the communication link, wherein the performing the benchmark testing with the client device comprises:
    - generating, a test array, the test array having a first size and being associated with a first timestamp;
    - compressing, using one of the set of compression algorithms, the test array to obtain a compressed test array, the compressed test array having a second size being associated with a second timestamp;
    - transmitting, to the client device, the compressed test array;
    - receiving, from the client device, an indication of a decompressed test data array, the indication of the test data array being associated with a third timestamp; and
    - determining, based on the first timestamp, the second timestamp, the third timestamp, the first size and the second size, the indication of the performance of the at least one of the client device and the communication link;
  - selecting, based on the indication of the performance of the at least one of the client device and the communication link, a given compression algorithm from a set of compression algorithms;
  - compressing, by using the given compression algorithm, a set of data arrays comprising a representation of the given image to obtain a set of compressed arrays; and
  - transmitting, to the client device, the set of compressed arrays, the set of compressed arrays comprising the representation of the given image to be generated for display on the client device.

12. The system of claim 11, wherein the determining the indication of the performance of the at least one of the client device and the communication link comprises:
   determining a transmission speed based on the second size, the third timestamp and the second timestamp;
   determining a compressed roundtrip time based on the third timestamp and the first timestamp; and
   determining an uncompressed roundtrip time based on the first size, the third timestamp and the first timestamp.

13. The system of claim 11, wherein the processor is further configured for, prior to said transmitting, to the client device, the set of compressed array comprising the representation of the given image:
   receiving past user interaction data from a database connected to the server; and
   selecting, based on the past user interaction data, the set of compressed arrays from the plurality of compressed arrays, the set of compressed arrays comprising a representation of at least one other image not having been explicitly requested by the client device.

14. The system of claim 13, wherein the past user interaction data comprises at least one of: past user interaction data of a user of the client device, past interaction data related to the given patient, and past interaction data related to similar medical imaging studies having been previously interacted with.

15. The system of claim 11, wherein the processor is further configured for:
   receiving, from the client device, a request for displaying a multi-dimensional visualization of at least a portion of the medical imaging study;
   determining, based on the request, a set of medical images required for generating the multi-dimensional visualization;
   transmitting, to the client device, at least a portion of a further set of data arrays, the further set of data arrays comprising a representation of the set of medical images required for generating the multi-dimensional visualization on the client device;
   determining a current performance of at least one of the client device and the communication link; and
   in response to the current performance of at least one of the client device and the communication link being below a performance threshold:
      generating the multi-dimensional visualization of the medical imaging study;
      generating a further data array comprising a representation at least one rendered frame of the multi-dimensional visualization of the medical imaging study; and
      transmitting, to the client device, the further data array comprising the representation of the at least one frame of the multi-dimensional visualization of the medical imaging study for display on the client device.

16. The system of claim 15, wherein the processor is further configured for:
   transmitting, to the client device, a remainder of the further set of data arrays, the transmitting thereby causing the client device to generate the multi-dimensional visualization of the medical imaging study using the further set of data arrays.

17. The system of claim 16, wherein the request for displaying the multi-dimensional visualization of the medical imaging study comprises a scene information and a camera setting; and wherein said determining the set of medical images required for generating the multi-dimensional visualization is based on the scene information and the camera setting.

18. The system of claim 15, wherein said transmitting, to the client device, at least the portion of the further set of data arrays comprises: compressing, by using the given compression algorithm, at least the portion of the further set of data arrays to obtain compressed further data arrays.

19. The system of claim 15, wherein said determining a current performance of at least one of the client device and the communication link respectively comprises: determining available computational resources on the client device, determining a transmission time, and determining a transmission speed.

20. The system of claim 11, wherein said transmitting, to the client device, the set of compressed arrays comprises marshalling the set of compressed arrays to obtain a set of binary serialized compressed arrays and transmitting the set of binary serialized compressed arrays to the client device.

21. A method for displaying a medical image on a client device connected to a server via communication link over communication network, the method comprising:
   receiving, by the server, a medical imaging study comprising a plurality of medical images having been acquired by a medical imaging apparatus for a given patient;
   generating, by the server, for each image of the plurality of images in the medical imaging study, a respective data array to obtain a plurality of data arrays;
   receiving, by the server from the client device, a request to display a given image of the medical image study;
   performing benchmark testing with the client device to obtain an indication of a performance of at least one of the client device and the communication link;
   selecting, based on the indication of the performance of the at least one of the client device and the communication link, a given compression algorithm from a set of compression algorithms;
   compressing, by using the given compression algorithm, a set of data arrays comprising a representation of the given image to obtain a set of compressed arrays;
   transmitting, to the client device, the set of compressed arrays, the set of compressed arrays comprising the representation of the given image to be generated for display on the client device;
   receiving, by the server, from the client device, a request for displaying a multi-dimensional visualization of at least a portion of the medical imaging study;
   determining, by the server, based on the request, a set of medical images required for generating the multi-dimensional visualization;
   transmitting, by the server to the client device, at least a portion of a further set of data arrays, the further set of data arrays comprising a representation of the set of medical images required for generating the multi-dimensional visualization on the client device;
   determining a current performance of at least one of the client device and the communication link; and
   in response to the current performance of at least one of the client device and the communication link being below a performance threshold:
      generating, by the server, the multi-dimensional visualization of the medical imaging study;

generating a further data array comprising a representation at least one rendered frame of the multi-dimensional visualization of the medical imaging study; and transmitting, by the server to the client device, the further data array comprising the representation of the at least one frame of the multi-dimensional visualization of the medical imaging study for display on the client device.

* * * * *